United States Patent [19]
Ullman et al.

[11] Patent Number: 6,143,514
[45] Date of Patent: *Nov. 7, 2000

[54] CHEMILUMINESCENT COMPOSITIONS AND THEIR USE IN THE DETECTION OF HYDROGEN PEROXIDE

[75] Inventors: Edwin F. Ullman, Atherton; Sharat Singh, San Jose, both of Calif.

[73] Assignee: Dade Behring Marburg GmbH, Marburg, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/850,026

[22] Filed: May 1, 1997

Related U.S. Application Data

[60] Provisional application No. 60/017,075, May 1, 1996.

[51] Int. Cl.[7] .............................. C12Q 1/28; C12Q 1/54
[52] U.S. Cl. .................................. 435/28; 435/6; 435/14; 435/177; 435/180
[58] Field of Search ..................................... 435/177, 180, 435/7.5, 7.9, 28, 14, 192, 6; 436/534, 528

[56] References Cited

U.S. PATENT DOCUMENTS

| | | | |
|---|---|---|---|
| 4,233,402 | 11/1980 | Maggio et al. | |
| 5,084,381 | 1/1992 | Akimoto et al. | |
| 5,332,662 | 7/1994 | Ullman | |
| 5,532,138 | 7/1996 | Singh et al. | |
| 5,536,834 | 7/1996 | Singh et al. | 544/98 |
| 5,556,758 | 9/1996 | Allen | |
| 5,578,498 | 11/1996 | Singh et al. | 436/518 |
| 5,616,719 | 4/1997 | Davalian et al. | 546/334 |
| 5,618,732 | 4/1997 | Pease et al. | 436/8 |
| 5,709,994 | 1/1998 | Pease et al. | 435/4 |

OTHER PUBLICATIONS

O'Connell, et al.; A Highly Sensitive Immunoassay System Involving Antibody–Coated Tubes and Liposome–Entrapped Dye; Clin. Chem.; 31/9:1424–1426; 1985.

Ullman, et al.; Luminescent oxygen channeling assay (LOCI™): sensitive, broadly applicable homogeneous immunoassay method; Clin. Chem.; 42/9:1518–1526; 1996.

Ullman, et al.; Luminescent oxygen channeling immunoassay: Measurement of particle binding kinetics by chemiluminescence; Proc. Natl. Acad. Sci. USA; 91:5426–5430; 1994.

McCapra, et al.; Luminescent Labels for Immunoassay–From Concept to Practice; Journal of Bioluminescence and Chemiluminescence; 4:51–58; 1989.

Seitz, Rudolf W.; Immunoassay Labels Based on Chemiluminescence and Bioluminescence; Clin. Biochemistry; 17:120–125; 1984.

Seliger, et al.; Chemiluminescence of Benzo[a]Pyrene–7, 8–Diol; Photochem. Photobiol.; 36:359–365; 1982.

Lee, et al.; Chemiluminescence from the Reaction of Singlet Oxygen with 10,10'–Dimethyl–9,9'–biacridylidene. A Reactive 1,2–Dioxetane; J. Org. Chem.; 41 No. 16:2685–2688; 1976.

Grayeski, Mary Lynn; Chemi– and Bioluminescence; edited by John G. Burr; Marcel Dekker, Inc.; 16:469–493; 1985.

McCapra, F.; Potential applications of bioluminescence and chemiluminescence in biosensors; Biosensors Fundamentals and Applications; No. 31:617–637; 1987.

McCapra, F. et al.; Selected Chemical Reactions That Produce Light; Bioluminescence and Chemiluminescence; Instruments and Applications; 1:9–42.

Poulsen, J.R., et al.; Solid–State Peroxyoxalate Chemiluminescence Detection of Hydrogen Peroxide Generated in a Post–Column Reaction; J. Chromatography; 360 No. 2:371–383; Jun. 25, 1986.

Wasserman, H.; et al.; Singlet Oxygen; Academic Press; No. 12:597–641; 1979.

E. Ullman et al, Clinical Chemistry, vol. 42, No. 9, pp. 1518–1526, 1996.

*Primary Examiner*—Mary E. Ceperley
*Attorney, Agent, or Firm*—Patrick G Gattari

[57] ABSTRACT

Compositions, methods and kits are disclosed. The compositions comprise a matrix having incorporated therein a label capable of being modified by singlet oxygen. A catalyst capable of catalyzing the formation of singlet oxygen is bound to the matrix, which permits the diffusion of singlet oxygen therein. The compositions may be used in methods for detecting hydrogen peroxide or a compound capable of generating hydrogen peroxide. A sample suspected of containing such compound is combined with a composition in accordance with the present invention. The combination is subjected to conditions wherein such compound generates hydrogen peroxide. The reaction of singlet oxygen with the label is determined, the reaction thereof indicating the presence of the compound capable of generating hydrogen peroxide.

47 Claims, No Drawings

CHEMILUMINESCENT COMPOSITIONS AND THEIR USE IN THE DETECTION OF HYDROGEN PEROXIDE

This application claims the benefit of U.S. Provisional Application No. 60/017,075 filed May 1, 1996.

BACKGROUND OF THE INVENTION

1. Field of the Invention

This invention relates to methods, compositions and kits for detecting hydrogen peroxide or a compound capable of generating hydrogen peroxide.

The clinical diagnostic field has seen a broad expansion in recent years, both as to the variety of materials of interest that may be readily and accurately determined, as well as the methods for the determination. Convenient, reliable and non-hazardous means for detecting the presence of low concentrations of materials in liquids is desired. In clinical chemistry these materials may be present in body fluids in concentrations below $10^{-12}$ molar. The difficulty of detecting low concentrations of these materials is enhanced by the relatively small sample sizes that can be utilized.

Detection of low concentrations of hydrogen peroxide is useful for numerous analytical procedures, particularly in clinical chemistry. Hydrogen peroxide is produced by cells such as monocytes and is an indicator of monocyte activation. Additionally, any material of interest that is or can be converted to a substrate for an oxidase such as xanthene oxidase, amino acid oxidase, NADH oxidase, glucose oxidase, galactose oxidase, glycerol phosphate oxidase, and the like can be detected by the hydrogen peroxide that is produced by the action of the enzyme on the substrate. Tests for glucose, triglycerides, d-amino acids, and cholesterol can be routinely carried out by detecting hydrogen peroxide, usually by reaction of a peroxidase and a chromogenic substrate. Enzyme immunoassays using an oxidase such as glucose oxidase as a label also depend on a sensitive detection method for hydrogen peroxide. For example, when glucose oxidase is used as a label, the hydrogen peroxide can be detected using horseradish peroxidase and a chromogenic substrate, or the hydrogen peroxide can be detected electrochemically.

Detection of hydrogen peroxide is also becoming more important in the area of foodstuffs. For example, in some countries hydrogen peroxide is used as a bleaching agent for food. It is important that residual levels of hydrogen peroxide in the food after bleaching be substantially zero to avoid health hazards.

A method that has higher sensitivity, less interference from the sample, and uses fewer, and more stable, reagents would increase the simplicity and reliability of assays for, or depending on, hydrogen peroxide detection.

Homogeneous immunoassays have previously been described for small molecules. These assays include Syva Company's FRAT® assay, EMIT® assay, enzyme channeling immunoassay, and fluorescence energy transfer immunoassay (FETI); enzyme inhibitor immunoassays (Hoffman LaRoche and Abbott Laboratories): fluorescence polarization immunoassay (Dandlicker), among others. All of these methods have limited sensitivity, and only a few including FETI and enzyme channeling, are suitable for large multi-epitopic analytes.

Luminescent compounds, such as fluorescent compounds and chemiluminescent compounds, find wide application in the assay field because of their ability to emit light. For this reason, luminescers have been utilized as labels in assays such as nucleic acid assays and immunoassays. For example, a member of a specific binding pair is conjugated to a luminescer and various protocols are employed. The luminescer conjugate can be partitioned between a solid phase and a liquid phase in relation to the amount of analyte in a sample suspected of containing the analyte. By measuring the luminescence of either of the phases, one can relate the level of luminescence observed to a concentration of the analyte in the sample.

Particles, such as liposomes and erythrocyte ghosts, have been utilized as carriers of encapsulated water soluble materials. For example, liposomes have been employed to encapsulate biologically active material for a variety of uses, such as drug delivery systems wherein a medicament is entrapped during liposome preparation and then administered to the patient to be treated.

Particles, such as latex beads and liposomes, have also been utilized in assays. For example, in homogeneous assays an enzyme may be entrapped in the aqueous phase of a liposome labeled with an antibody or antigen. The liposomes are caused to release the enzyme in the presence of a sample and complement. Antibody or antigen-labeled liposomes, having water soluble fluorescent or non-fluorescent dyes encapsulated within an aqueous phase vesicle or lipid soluble dyes dissolved in the lipid bilayer of a lipid, have also been utilized to assay for analytes capable of entering into an immunochemical reaction with the surface bound antibody or antigen. Detergents have been used to release the dyes from the aqueous phase of the liposomes.

2. Brief Description of the Related Art

U.S. Pat. No. 5,084,381 (Akimoto, et al.) discusses an assay method for detecting hydrogen peroxide.

Processes and materials for carrying out specific binding assays is disclosed in patent application WO 86/01899 (Davis, et al.).

U.S. Pat. No. 5,108,893 (Baret) discloses the use of oxidase enzyme systems in chemiluminescent assays.

European Patent Application 0 421 788 A2 (Allen) discloses a haloperoxidase-acid-oxidant chemiluminescence assay system for determining the presence or amount of an analyte in a liquid sample.

U.S. Pat. No. 4,315,998 discusses polymer-bound photosensitizing catalysts.

Photoactivatable chemiluminescent matrices are described in patent application WO 94/03812 (Pease, et al.).

European Patent Application No. 0 515 194 A2 discloses assay methods utilizing induced luminescence. The references cited therein are incorporated herein by reference including without limitation U.S. Pat. No. 5,017,473 (Wagner), which discloses a homogeneous chemiluminescence immunoassay using a light absorbing material, European Patent Application No. 0,345,776 (McCapra), which discloses specific binding assays that utilize a sensitizer as a label, U.S. Pat. No. 4,193,983 (Ullman, et al.), which discloses labeled liposome particle compositions and immunoassays therewith, U.S. Pat. No. 4,891,324 (Pease, et al.), which describes a particle with luminescer for assays.

SUMMARY OF THE INVENTION

In its broadest aspect the present invention concerns compositions comprising a matrix having incorporated therein a label capable of being modified by singlet oxygen. A catalyst capable of catalyzing the formation of singlet oxygen is bound or attached to the surface of the matrix, which permits the diffusion of singlet oxygen therein.

Another aspect of the invention is a composition comprising a matrix selected from the group consisting of latex polymers and lipid bilayers. The matrix has incorporated therein a label capable of being activated by singlet oxygen. A peroxidase is bound to the surface of the matrix, which permits the diffusion of singlet oxygen therein.

Another aspect of the present invention is a method for detecting hydrogen peroxide or a compound capable of generating hydrogen peroxide. A combination is provided comprising (i) a sample suspected of containing hydrogen peroxide or such compound capable of generating hydrogen peroxide and (ii) a composition comprising a matrix having incorporated therein a label capable of being activated by singlet oxygen. A catalyst capable of catalyzing the formation of singlet oxygen from hydrogen peroxide is bound to the matrix, which permits the diffusion of singlet oxygen therein. The combination is subjected to conditions wherein such catalyst generates singlet oxygen. The luminescence produced by reaction of singlet oxygen with the label is determined. The reaction thereof indicates the presence of such compound.

Another aspect of the present invention is a method for detecting hydrogen peroxide or a substance capable of generating hydrogen peroxide. A combination is provided comprising (i) a sample suspected of containing hydrogen peroxide or a substance capable of generating hydrogen peroxide and (ii) a composition comprising a matrix having incorporated therein a label capable of being activated by singlet oxygen. A catalyst capable of catalyzing the conversion of hydrogen peroxide to singlet oxygen is bound or attached to the surface of the matrix, which permits the diffusion of singlet oxygen therein. The combination is subjected to conditions wherein hydrogen peroxide reacts with the catalyst to form singlet oxygen. A determination is made as to whether singlet oxygen has reacted with the label. The extent of reaction thereof indicates the presence or amount of hydrogen peroxide or of said substance in the sample.

Another embodiment in accordance with the present invention is a method for detecting hydrogen peroxide or a substance capable of generating hydrogen peroxide. A combination is provided comprising (i) a sample suspected of containing hydrogen peroxide or a substance capable of generating hydrogen peroxide and (ii) a composition comprising a matrix selected from the group consisting of latex polymers and lipid bilayers. The matrix has incorporated therein an olefin capable of reaction with singlet oxygen. A peroxidase is bound to the surface of the matrix, which permits the diffusion of singlet oxygen therein. The combination is subjected to conditions wherein hydrogen peroxide reacts with the peroxidase to form singlet oxygen and, then, a determination is made as to whether singlet oxygen has reacted with the olefin. The reaction thereof indicates the presence of hydrogen peroxide or of the substance in the sample.

Another aspect of the present invention is a method for detecting an analyte, which is a member of a specific binding pair (sbp). A combination is provided comprising (i) a sample suspected of containing the analyte, (ii) an sbp member bound to either an oxidase or a peroxidase, the sbp member being capable of binding to the analyte or to an sbp member capable of binding to the analyte, (iii) a composition comprising a matrix having incorporated therein a label capable of being modified by singlet oxygen, (iv) the other of an oxidase or a peroxidase bound to the matrix or bound to an sbp member capable of binding to the matrix (i.e., an oxidase is bound to the matrix if the sbp member of (ii) above is bound to a peroxidase or a peroxidase is bound to the matrix if the sbp member of (ii) above is bound to an oxidase), wherein the matrix permits the diffusion of singlet oxygen therein, and (v) a substrate for the oxidase capable of generating hydrogen peroxide upon reaction with the oxidase. The combination is incubated in a medium under conditions sufficient to allow the sbp members to bind and the substrate for the oxidase to react with the oxidase. A determination is made as to whether singlet oxygen has reacted with the label. The extent of such reaction is related to the presence and/or amount of the analyte in the sample.

Another embodiment of the present invention is a kit comprising in packaged combination (a) a composition comprising a matrix having incorporated therein a label capable of being modified by singlet oxygen, wherein an enzyme capable of catalyzing the conversion of hydrogen peroxide to singlet oxygen is bound to the matrix or, if not so bound, is bound to an sbp member that is capable of binding to the matrix and the matrix permits the diffusion of singlet oxygen therein and (b) a substrate for the enzyme other than hydrogen peroxide.

Another embodiment of the present invention is a kit comprising in packaged combination (a) a composition comprising a matrix and a label capable of being modified by singlet oxygen, (b) a peroxidase and (c) an oxidase. The peroxidase and the oxidase are bound to, or capable of becoming bound to, the matrix.

DESCRIPTION OF THE SPECIFIC EMBODIMENTS

In one aspect the present invention utilizes the formation of singlet oxygen from hydrogen peroxide to permit detection of hydrogen peroxide with minimal interference from a sample. A catalyst is bound to the surface of a matrix that is insoluble in an assay medium and that has a label such as a chemiluminescent material incorporated therein. The catalyst is capable of directly or indirectly causing the production of singlet oxygen by causing the conversion of hydrogen peroxide. The invention finds application in the detection of hydrogen peroxide, which may be present due to its addition to a medium or its formation as a reaction product, for example, in the detection of an analyte. In this latter regard the present invention finds use in assays for the detection and measurement of a wide variety of analytes in a simple, efficient and reproducible manner, which can employ visual inspection or conventional equipment for measuring the amount of light produced during the reaction.

Before proceeding further with a description of the specific embodiments of the present invention, a number of terms will be defined and described in detail.

Label capable of being modified by singlet oxygen—a substance that in the presence of singlet oxygen undergoes a detectable change such as, for example, a reaction with singlet oxygen to form a different substance such as a fluorescent or chemiluminescent substance or a precursor thereto. Examples of such labels, by way of illustration and not limitation, are olefins capable of reacting with singlet oxygen to form, e.g., hydroperoxides or dioxetanes, acetylenes that can react with singlet oxygen to form diketones, hydrazones or hydrazides that can form azo compounds or azo carbonyls, aromatic compounds that can form endoperoxides, etc. The labels can produce any detectable signal upon reaction with singlet oxygen either directly or by way of subsequent reaction of the initial reaction product. The signal with usually be initiated by and/or detected as electromagnetic radiation and will preferably be chemiluminescence, fluorescence or phosphorescence.

Olefins capable of reaction with singlet oxygen—a typical reaction of olefins with singlet oxygen is 2+2 addition to form a dioxetane. These olefins include, by way of illustration and not limitation, chemiluminescent and fluorescent olefin precursors. Dioxetanes can dissociate spontaneously or by heating with spontaneous chemiluminescence, or the carbonyl groups that are formed can be formed as part of a fluorescent group or be capable of undergoing subsequent reactions that lead to a fluorescent molecule. Alternatively, this dissociation reaction can lead to separation of a quenching group from a fundamentally fluorescent group that thereby regains its fluorescent property.

In the above olefin reactions the rate of bond breaking is often faster if the olefin is substituted with electron donating groups such as ethers, thioethers, amines, and the like.

Another type of reaction of singlet oxygen with olefins is 4+2 cycloaddition with dienes, usually aromatic compounds such as naphthalenes and naphthacenes. Such a reaction leads initially to an endoperoxide. In some cases endoperoxides can rearrange to active esters or anhydrides that are capable of reaction with a suitably placed group to provide a lactone or lactam that can be fluorescent. Alternatively, the endoperoxides may oxidize a fluorescent or chemiluminescent compound precursor. Endoperoxides can also dissociate spontaneously or on heating with chemiluminescent emission.

Still another type of reaction of singlet oxygen with olefins is the "ene" reaction that produces an allylhydroperoxide. This product can react with an active ester in the same molecule to form a dioxetanone that can spontaneously or by heating dissociate with chemiluminescent emission.

Chemiluminescent olefin (CC)—an olefinic substance that undergoes a chemical reaction upon reaction with singlet oxygen to form a metastable reaction product, usually a dioxetane or endoperoxide, which is capable of decomposition with the simultaneous or subsequent emission of light, usually within the wavelength range of 250 to 1200 nm. CC's that are preferred in the present invention are those that react with singlet oxygen to form dioxetanes. Preferred CC's are electron rich olefins. Exemplary of such electron rich olefins are enol ethers, enamines, 9-alkylidene-N-alkylacridans, arylvinylethers, 1,4-dioxenes, 1,4-thioxenes, 1,4-oxazines, arylimidazoles, 9-alkylidene-xanthenes and lucigenin.

The CC's of interest will preferably emit at a wavelength above 300 nanometers, preferably above 500 nanometers, and more preferably above 550 nm. Compounds that absorb and emit light at wavelengths beyond the region where the sample components contribute significantly to light absorption will be of particular use in the present invention. The absorbance of serum drops off rapidly above 500 nm and becomes insignificant above 600 nm. Chemiluminescent olefins that emit light above 550 nm are of particular interest. However, chemiluminescent olefins that absorb at shorter wavelengths are useful when interference absorbance of the sample is absent. Preferably, the chemiluminescent olefins will absorb light at less than about 400 nm to permit convenient handling in room light without the risk of inadvertently producing singlet oxygen by photosensitization.

Where long wave length emission from the chemiluminescent olefin is desired, a long wavelength emitter such as an oxazine dye bound to the chemiluminescent olefin can be used. Alternatively, a fluorescent molecule can be included in the medium containing the chemiluminescent olefin. Preferred fluorescent molecules will be excited by the activated chemiluminescent olefin and emit at a wavelength longer than the emission wavelength of the chemiluminescent olefin, usually greater that 550 nm. Examples of useful dyes include rubrene, bis-phenylethynylanthracene, phthalocyanine, bis-(4-diimethlyaminophenyl)squaraine, dansyl, $Eu(fod)_3$, $Eu(TTA)_3$, etc. In general these dyes act as acceptors in energy transfer processes and preferably have high fluorescent quantum yields and do not react rapidly with singlet oxygen. They can be incorporated into particles together with the chemiluminescent olefin into the particles. The CC's generally do not contain chemically reactive allylic CH or NH groups.

Examples of suitable electron rich chemiluminescent olefins are set forth in U.S. patent application Ser. No. 07/923,069, abandoned, at page 64, line 8, to page 76, line 11, the disclosure of which is incorporated herein by reference. Such olefins generally have an electron donating group in conjugation with the olefin.

The more preferred olefins are those that yield a dioxetane that decays rapidly at room temperature (less than 60 minutes, preferably less than 5 minutes, desirably less than 30 sec). The dioxetanes may be luminescent alone or in conjunction with a fluorescent energy acceptor. Enol ethers are examples of such olefins. Frequently, the enol ether compounds will have at least one aryl group bound to the olefinic carbons where the aryl ring is substituted with an electron donating group at a position that increases the reactivity of the olefin to singlet oxygen and/or imparts fluorescence to the product of dissociation of the resultant dioxetane. The electron donating group can be, for example, hydroxyl, alkoxy, disubstituted amino, alkyl thio, furyl, pyryl, etc. Preferably, the enol ethers have an electron-donating group bound directly to an olefinic carbon.

Enamines are another example of such olefins. In general, useful enamines will be governed by the rules set forth above for enol ethers.

Another family of CC's is the 2,4,5-triphenylimidazoles, with lophine as the common name for the parent product. Chemiluminescent analogs include para-dimethylamino and -methoxy substituents.

Other chemiluminescent olefins that satisfy the requirements given above may be found in European Patent Application No. 0,345,776.

Some of the dioxetanes decompose spontaneously, others by heating, with the emission of light.

Fluorescent compound precursor—refers to compounds that react with singlet oxygen to form a fluorescent compound or a compound that can react with an auxiliary compound that is thereupon converted to a fluorescent compound. There are several types of reactions of singlet oxygen that can give compounds that will lead to a fluorescent compound. The type of reaction that is employed and the choice of the fluorescent compound that is desired provides a guide to the structures of the fluorescent compound precursors and any auxiliary compounds used in the present invention.

The fluorescent compound precursor will preferably undergo a reaction with singlet oxygen that is very rapid, usually at least $10^4$–$10^6$ $sec^{-1}$, preferably at least $10^6$–$10^8$ $sec^{-1}$, more preferably $>10^8$ $sec^{-1}$. When the initial product of the reaction is an intermediate that reacts to give a fluorescent compound, the intermediate will preferably have a lifetime that is short relative to the desired time between forming singlet oxygen and detecting the fluorescence emitted from the fluorescent compound upon exposure to light. For simultaneous singlet oxygen generation and fluorescence detection the lifetime is usually shorter than the total measurement period, preferably, at least 10-fold shorter. When generation of singlet oxygen and fluorescence detection are sequential, the lifetime is usually shorter than the intervening period between generation of singlet oxygen and detection, preferably, at least 10-fold shorter.

Higher rates of reaction of singlet oxygen are achieved by providing singlet oxygen reactive groups in the fluorescent compound precursor that are electron rich. These groups will usually be an olefin or acetylene, hydrazine and hydroxylamine derivatives, selenides and tellurides but are not limited to these groups. For example, alkyl tellurides having a β-hydrogen atom have been found to be particularly useful because they react rapidly with singlet oxygen to produce an olefin. The reaction rate depends on the electron availability (oxidation potential) of the tellurium. For example, electron donating groups on an aryl ring substituent on the tellurium atom can increase the rate of reaction. Changing from tellurium to selenium (the next lower chalcogenide) will decrease the rate, but increase the stability of the molecule toward spontaneous oxidation.

When the fluorescent compound precursor contains a hydrazine or hydrazide, reaction with singlet oxygen can produce a double bond. For example, singlet oxygen can convert hydrazides directly into fluorescent compounds as in the conversion of 1,2-indazoline-3-one into 1,2-indazol-3-one. The oxidation potential of a hydrazine is an important factor in providing a high rate of reaction. Electron withdrawing groups such as an acyl group (e.g., as in a hydrazide) slow the reaction although acyl hydrazides and diacyl hydrazides can still be used as fluorescent compound precursors in the present invention.

Still another example of a useful singlet oxygen reaction is the reaction with electron rich olefins such as those described in European Published Patent Application No. 0 515 194. Two fundamental types of reactions are described. One of these is the "ene" reaction which shifts the position of a double bond and produces a hydroperoxide. The double bond shift can cause two auxochromic groups in the fluorescent compound precursor to come into conjugation and thus produce a fluorescent compound.

Other fluorescent compound precursors react with singlet oxygen to form hydroperoxides which can react internally with an oxidizable group to give a fluorescent compound. Alternatively, a hydroperoxide formed by reaction of singlet oxygen with a fluorescent compound precursor, such as 1,3-diphenylpropene, can serve to oxidize the leuco form of a dye which is present as an auxiliary compound so as to form a fluorescent compound. The hydroperoxide can also oxygenate a group V element in an auxiliary compound to cause it to cease to act as an electron-donating quencher of an associated fluorescent group. The auxiliary compound could alternatively have a selenium or tellurium atom that could react with a hydroperoxide to produce an intermediate that could undergo subsequent elimination to form a fluorescent compound.

The structure of the fluorescent compound precursor will therefore depend on the particular singlet oxygen reaction that is to be employed and it will usually be designed to assure that any subsequent reactions initiated by reaction with singlet oxygen that are required to produce a fluorescent compound will proceed relatively rapidly. Additionally, the structure of the fluorescent compound precursor will lead to the formation of a fluorescent compound that has the desired absorption and emission wavelengths and has relatively high fluorescent quantum yields, preferably >0.1, more preferably greater than 0.4, and a high extinction coefficient at the desired excitation wavelength, preferably>1000 $M^{-1}$ $cm^{-1}$, more preferably>10,000 $M^{-1}$ $cm^{-1}$.

Particularly preferred within these compounds are those compounds containing a tellurium.

Other classes of fluorescent compound precursors can also be used in the present invention. For example, compounds that produce chemiluminescence on reaction with singlet oxygen are frequently converted to fluorescent products which can serve as fluorescent compounds of the present invention.

Examples, by way of illustration and not limitation, of fluorescent compound precursors that may be utilized in the present invention are

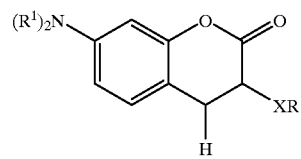

wherein X is a selenium or tellurium, R is an organic or organometallic group bound to X through an unsaturated carbon atom, a silicon atom, or a tin atom; and $R^1$ is hydrogen or alkyl; and wherein up to four of the remaining hydrogen atoms may be replaced by alkyl or alkylene substituents which may be taken together to form one or more alicyclic or aromatic rings. Examples of such compounds where X is tellurium and the fluorescent photoactive indicator molecule formed upon the compounds' reaction with singlet oxygen are given below:

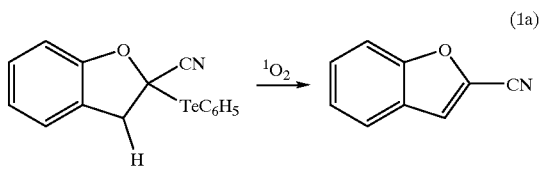
(1a)

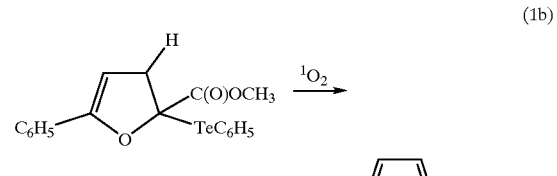
(1b)

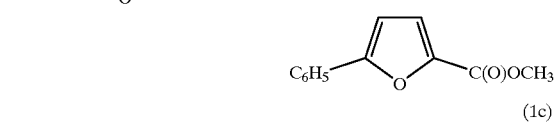

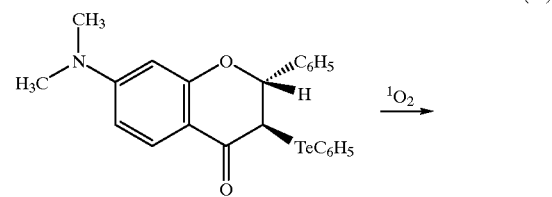
(1c)

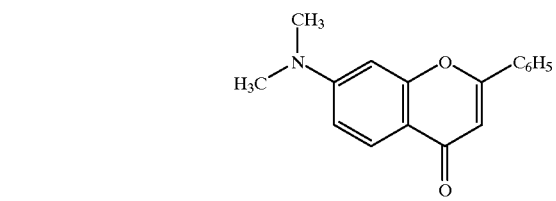

-continued

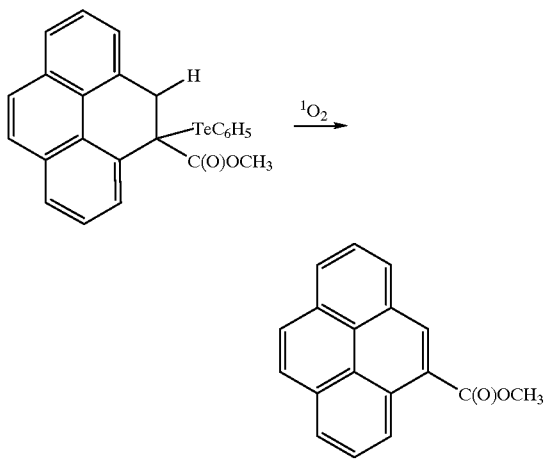

(1d)

The phenyltelluridyl radical (—TeC$_6$H$_5$) in these compounds can be replaced with other tellurium derivatives, such as TeSiC(CH$_3$)$_3$ and TeSn((CH$_2$)$_3$CH$_3$)$_3$, or the phenyl group can be substituted, preferably with electron donating groups such as —N(CH$_3$)$_2$ and —)OCH$_3$. When X is selenium it is preferable that the selenium is substituted by a strong electron donor group or atom, such as tin.

Other classes of photoactive indicator precursors can also be used in the present invention. For example, compounds that chemiluminesce on reaction with singlet oxygen are frequently converted to fluorescent products which can serve as photoactive indicators of the present invention. Examples of such photoactive indicator precursors and the photoactive indicators produced upon reaction with singlet oxygen include the following:

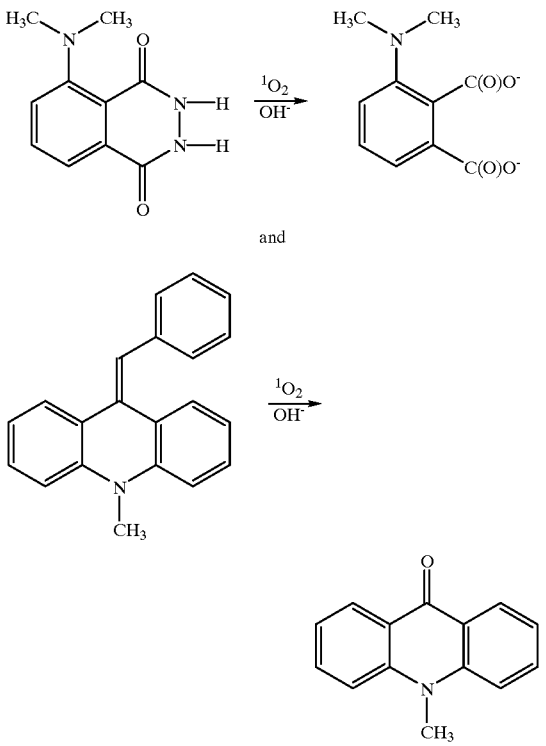

Fluorescent compound—refers to a molecule which, following absorption of light of wavelengths of 250 to 1100 nm, preferably 300 to 950 nm, emits light by fluorescence or phosphorescence, preferably by fluorescence, or transfers its excitation energy to an acceptor molecule which thereupon emits light by fluorescence or phosphorescence. Preferably the emission quantum yield will be high, usually at least 0.1, preferably at least 0.4, more preferably greater than 0.7 and the extinction coefficient of the absorption maximum will usually be greater than 5000 M$^{-1}$cm$^{-1}$.

Typical fluorescent compounds include, for example, fluorescent brighteners, which typically absorb light between 300 and 400 nanometers and emit between 400 and 500 nanometers; xanthenes such as rhodamine and fluorescein; bimanes; coumarins such as umbelliferone; aromatic amines such as dansyl; squarate dyes; benzofurans; cyanines, merocyanines, rare earth chelates, and the like. Phosphorescent compounds include porphyrins, phthalocyanines, polyaromatic compounds such as pyrene, anthracene and acenaphthene.

Compound capable of generating hydrogen peroxide—any substance other than molecular oxygen that is capable of producing hydrogen peroxide either directly or through the formation of one or more intermediates capable of producing hydrogen peroxide. Compounds that can be converted to, or can catalyze the formation of, hydrogen peroxide or exist as, or can be converted to, a catalyst for the formation of hydrogen peroxide can be detected as analytes in the method of this invention and are included in the above definition of "compounds capable of generating hydrogen peroxide."

For example, the present invention can be utilized to detect enzymes such as phosphatase, amylase, cholinesterase, creatinine kinase, and the like, and enzyme substrates such as glucose, cholesterol, creatinine, uric acid, and the like. The following discussion illustrates, by way of example and not limitation, the above, wherein H$_2$O$_2$ is produced either directly or indirectly through the formation of one or more intermediate products in a system that ultimately produces H$_2$O$_2$:

1) Amylase catalyzes the reaction of its substrate starch to form the intermediate product glucose, a substrate for glucose oxidase (1.1.3.4), which in the presence of molecular oxygen catalyzes the conversion of glucose to gluconic acid wherein H$_2$O$_2$ also produced.

2) Cholinesterase catalyzes the reaction of its substrate acetylcholine to form the intermediate product choline, a substrate for choline oxidase (1.1.3.17), which catalyzes the conversion of choline to trimethyl ammonium acetaldehyde wherein H$_2$O$_2$ is also produced.

3) Creatinine kinase catalyzes the reaction of its substrate creatinine in the presence of adenosine diphosphate (ADP) to form the intermediate product adenosine triphosphate (ATP), which in the presence of hexokinase causes the conversion of glucose to the intermediate glucose-6-phosphate (G-6-P), which in turn is a substrate for the enzyme glucose-6-phosphate dehydrogenase (G-6-PDH), wherein NAD is converted to the intermediate NADH during the catalytic reaction of G-6-P with G-6-PDH; H$_2$O$_2$ and NAD are produced in the reaction of NADH-FMN oxidoreductase (1.6.99.3) with NADH.

4) Phosphatase catalyzes the reaction of its substrate CH$_3$CH$_2$OPO$_3$H$_2$ to form the intermediate product ethanol, which in turn is a substrate for the enzyme alcohol dehydrogenase (ADH), wherein NAD is converted to the intermediate product NADH during the catalytic reaction of ethanol with ADH to form acetaldehyde; H$_2$O$_2$ and NAD are produced in the reaction of NADH-FMN oxidoreductase (1.6.99.3) with NADH.

5) In the catalytic reaction of lactate dehydrogenase with its substrate lactate in the presence of NAD the intermediate product NADH is formed; $H_2O_2$ and NAD are produced in the reaction of NADH-FMN oxidoreductase (1.6.99.3) with NADH.
6) Glucose is an enzyme substrate for glucose oxidase (1.1.3.4), the products being gluconic acid and $H_2O_2$.
7) Cholesterol is an enzyme substrate for cholesterol oxidase, $H_2O_2$ being formed during the reaction.
8) Creatinine is an enzyme substrate for creatinine amidinehydrolase, which produces the intermediate product sarcosine, which in turn is an enzyme substrate for the enzyme sarcosine oxidase (1.5.3.1), the products being formaldehyde and $H_2O_2$.
9) Uric acid is an enzyme substrate for uricase, $H_2O_2$ being formed during the catalytic reaction.

Hydrogen peroxide is also produced by certain types of cells and, thus, the present invention permits the detection of hydrogen peroxide as an indicator of cellular activity.

Hydrogen peroxide is also produced by substrates for oxidase enzymes in the catalyzed reaction of the substrate with molecular oxygen. In such a reaction the substrate is oxidized and is the hydrogen donor and molecular oxygen is the acceptor. Such substrates and their corresponding oxidases include, by way of illustration and not limitation, the following:

molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase,

| Substrate | Enzyme | Products |
| --- | --- | --- |
| xanthene | xanthene oxidase (1.1.3.22) | uric acid + $H_2O_2$ |
| D-amino acids | D-amino acid oxidase (1.4.33) | α-keto acid + $H_2O_2$ |
| L-amino acids | L-amino acid oxidase (1.4.3.2) | α-keto acid + $H_2O_2$ |
| NADH | NADH-FMN oxidoreductase (1.6.99.3) | NAD + $H_2O_2$ |
| glucose | glucose oxidase (1.1.3.4) | gluconic acid + $H_2O_2$ |
| galactose | galactose oxidase (1.1.3) | galactonic acid + $H_2O_2$ |
| glycerol-1-phosphate | glycerol phosphate oxidase (1.1.3.21) | dihydroxyacetone phosphate + $H_2O_2$ |
| sarcosine | sarcosine oxidase (1.5.3.1) | formaldehyde + $H_2O_2$ |
| choline | choline oxidase (1.1.3.17) | trimethyl ammonium acetalaldehyde + $H_2O_2$ |
| ethanol | alcohol oxidase (1.1.3.13) | formaldehyde + $H_2O_2$ |

Analyte—the compound or composition to be detected, which includes hydrogen peroxide or a compound capable of generating hydrogen peroxide.

The term "analyte" also includes compounds or compositions, other than hydrogen peroxide or a compound capable of generating hydrogen peroxide, the detection of which involves the use of a signal producing, e.g., enzyme, system wherein hydrogen peroxide is formed. The analyte can be comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen or a microorganism, e.g., bacterium, fungus, protozoan, or virus.

The polyvalent ligand analytes will normally be poly (amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a myoglobin, CPK-MB and calcitonin, and peptide hormones. Other polymeric materials of interest are mucopolysaccharides and polysaccharides.

The monoepitopic ligand analytes will generally be from about 100 to 2,000 molecular weight, more usually from 125 to 1,000 molecular weight. The analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The next group of drugs includes steroids, which includes the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g. phenobarbital and secobarbital, diphenylhydantoin, primidone, ethosuximide, and their metabolites.

The next group of drugs is aminoalkylbenzenes, with alkyl of from 2 to 3 carbon atoms, which includes the amphetamines; catecholamines, which includes ephedrine, L-dopa, epinephrine; narceine; papaverine; and metabolites of the above.

The next group of drugs is benzheterocyclics which include oxazepam, chlorpromazine, tegretol, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs is the hormones such as thyroxine, cortisol, triiodothyronine, testosterone, estradiol, estrone, progestrone, polypeptides such as angiotensin, LHRH, and immunosuppresants such as cyclosporin, FK506, mycophenolic acid, and so forth.

The next group of drugs includes the vitamins such as A, B, e.g. B12, C, D, E and K, folic acid, thiamine.

The next group of drugs is prostaglandins, which differ by the degree and sites of hydroxylation and unsaturation.

The next group of drugs is the tricyclic antidepressants, which include imipramine, dismethylimipramine, amitriptyline, nortriptyline, protriptyline, trimipramine, chlomipramine, doxepine, and desmethyldoxepin, The next group of drugs are the anti-neoplastics, which include methotrexate.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

The analyte may be a molecule found directly in a sample such as biological tissue, including body fluids, from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The biological tissue includes excised tissue from an organ or other body part of a host and body fluids, for example, urine, blood, plasma, serum, saliva, semen, stool, sputum, cerebral spinal fluid, tears, mucus, and the like.

Catalyst capable of catalyzing the formation of singlet oxygen—a substance that can directly or indirectly catalyze the conversion of hydrogen peroxide to singlet oxygen, usually, an enzyme. Examples of such catalysts are, by way of illustration and not limitation, enzymes such as peroxidases or enzymes having peroxidase activity, such as lactoperoxidase, haloperoxidase, metals such as platinum, and transition metals such as tungstate, titanate, vanadate and molybdate salts and lanthanide oxides, e.g., europium oxide, ytterbium oxide and so forth.

Certain enzymes require a substrate other than hydrogen peroxide to induce formation of singlet oxygen. Accordingly, such a substrate should be included in an assay medium. For example, chloride or bromide ions are known substrates for haloperoxidases and lactoperoxidase and are enzymatically oxidized by hydrogen peroxide to chlorine and bromine, respectively. The resulting halogens are known to react further with hydrogen peroxide to give singlet oxygen. Other peroxidase substrates that can cause formation of singlet oxygen can in principal be used.

Matrix—a support comprised of an organic or inorganic, solid or fluid, water insoluble material, which may be transparent or partially transparent. The primary requirement of the matrix is that it permit the diffusion of singlet oxygen therein at least to the proximate location of the incorporated label. It is preferable that the matrix also exclude components of the sample that may react with singlet oxygen or affect the signal from the CC or the fluorescent compound. The matrix can have any of a number of shapes, such as particle, including bead, film, membrane, tube, well, strip, rod, and the like. The surface of the matrix is, preferably, hydrophilic or capable of being rendered hydrophilic. The body of the matrix is, preferably, hydrophobic. The matrix may be suspendible in the medium in which it is employed. Examples of suspendible matrices in accordance with the present invention, by way of illustration and not limitation, are polymeric materials such as latex, lipid bilayers, oil droplets, cells and hydrogels. Other matrix compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials.

Binding of the catalyst and, where appropriate, sbp members to the matrix may be direct or indirect, covalent or non-covalent and can be accomplished by well-known techniques, commonly available in the literature. See, for example, "Immobilized Enzymes," Ichiro Chibata, Halsted Press, New York (1978) and Cuatrecasas, *J. Biol Chem.*, 245:3059 (1970).

The surface of the matrix will usually be polyfunctional or be capable of being polyfunctionalized or be capable of binding to a catalyst, an sbp member, or the like through specific or non-specific covalent or non-covalent interactions. Such binding is indirect where specific, non-covalent interactions are used and is direct where covalent interactions are employed. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well known and is amply illustrated in the literature (see above). The length of a linking group to the oligonucleotide or sbp member may vary widely, depending upon the nature of the compound being linked, the effect of the distance between the compound being linked and the surface on the specific binding properties and the like.

The amount of catalyst bound to the surface of the matrix is dependent on a number of factors including the nature of the catalyst and the intended use of the composition. The catalyst is present on the matrix in an amount selected empirically to provide the highest signal to background in an assay. Since the label may have background signal, it may be desirable to have a high ratio of catalyst to the label compound, particularly when a fluorescer precursor is used. Relatively high amounts of catalyst also increase the rate/sensitivity of the assay, but cost and undesirable surface properties may provide limits with some catalysts. The surface density of the catalyst on the matrix is generally in the range of from about $10^8$ to $10^{14}$ molecules per square centimeter, usually $10^9$ to $10^{12}$ molecules per square centimeter.

As mentioned above, a label is incorporated in the matrix. The label may be incorporated into the matrix either during or after the preparation of the matrix. The label is usually chosen to dissolve in the matrix but may be covalently attached to the matrix. The label compounds are usually hydrophobic to reduce their ability to dissociate from the matrix. In general the matrix composition is chosen so as to favor association of the label with the matrix. The amount of label incorporated into the matrix in the compositions of the invention depends upon a number of factors such as the nature of the label and the matrix and the intended use of the composition. The label is present in the matrix in an amount necessary to maximize the signal produced in accordance with the invention, i.e., to provide the highest signal to background in an assay. Generally, the amount of label is determined empirically and is usually about from $10^{-8}$ to 5M, preferably, from $10^{-5}$ to $10^{-2}$ M, more preferably, $10^{-3}$ to $10^{-1}$ M.

The surface density of the sbp member on the matrix is generally in the range of from about $10^8$ to $10^{14}$ molecules per square centimeter, usually $10^9$ to $10^{12}$ molecules per square centimeter. The particular amount of sbp member is also dependent on a number of factors and is usually best determined empirically.

Particles—particles of at least about 20 nm and not more than about 20 microns, usually at least about 40 nm and less than about 10 microns, preferably from about 0.10 to 2.0 microns diameter, normally having a volume of less than 1 picoliter. The particle may have any density, but preferably of a density approximating water, generally from about 0.7 to about 1.5 g/ml. The particles may or may not have a charge, and when they are charged, they are preferably negative. The particles may be solid (e.g., comprised of organic and inorganic polymers or latex), oil droplets (e.g., hydrocarbon, fluorocarbon, silicon fluid), or vesicles (e.g., synthetic such as phospholipid or natural such as cells and organelles).

The solid particles are normally polymers, either addition or condensation polymers, which are readily dispersible in the assay medium. The solid particles will also be adsorptive or functionalizable so as to bind or attach at their surface, either directly or indirectly, an sbp member and to incorporate within their volume a label capable of being modified by singlet oxygen such as a chemiluminescent olefin.

The solid particles can be comprised of polystyrene, polyacrylamide, homopolymers and copolymers of derivatives of acrylate and methacrylate, particularly esters and amides, silicones and the like.

The particles are normally bound or attached to a catalyst and, in some instances, to an sbp member as described above.

Oil droplets—are water-immiscible fluid particles comprised of a lipophilic compound coated and stabilized with an emulsifier that is an amphiphilic molecule such as, for example, phospholipids, sphingomyelin, albumin and the like that exist as a suspension in an aqueous solution, i.e. an emulsion.

The phospholipids are based upon aliphatic carboxylic acid esters of aliphatic polyols, where at least one hydroxylic group is substituted with a carboxylic acid ester of from about 8 to 36, more usually of from about 10 to 20 carbon atoms, which may have from 0 to 3, more usually from 0 to 1 site of ethylenic unsaturation and at least 1, normally only 1, hydroxyl group substituted with phosphate to form a phosphate ester. The phosphate group may be further substituted with small aliphatic compounds which are difunctional or of higher functionality, generally having hydroxyl or amino groups.

Emulsions comprising oil droplets can be made in accordance with conventional procedures by combining the appropriate lipophilic compounds with a surfactant, anionic, cationic or nonionic, where the surfactant is present in from about 0.1 to 5, more usually from about 0.1 to 2 weight percent of the mixture and subjecting the mixture in an aqueous medium to agitation, such as sonication or vortexing. Illustrative lipophilic compounds include hydrocarbon oils, halocarbons including fluorocarbons, alkyl phthalates, trialkyl phosphates, triglycerides, etc.

A catalyst will usually be adsorbed to the surface of the oil droplet or bonded directly or indirectly to a surface component of the oil droplet.

The following is a list, by way of illustration and not limitation, of amphiphilic compounds, which may be utilized for stabilizing oil droplets: phosphatidyl ethanolamine, phosphatidyl choline, phosphatidyl serine, dimyristoylphosphatidyl choline, egg phosphatidyl choline, dipalmitoylphosphatidyl choline, phosphatidic acid, cardiolipin, lecithin, galactocerebroside, sphingomyelin, dicetylphosphate, phosphatidyl inositol, 2-trihexadecylammoniumethylamine, 1,3-bis(octadecyl phosphate)-propanol, stearoyloxyethylene phosphate, phospholipids, dialkylphosphates, sodium dodecyl sulfate, cationic detergents, anionic detergents, proteins such as albumin, non-ionic detergents, etc.

Other compounds may also be used which have lipophilic groups and which have been described previously. For the most part, these compounds have a lipophilic component such as an alkylbenzene, having alkyl groups of from 6 to 20 carbon atoms, usually mixtures of alkyl groups, which may be straight or branched chain, and a hydrophilic component such as a carboxyl group, an hydroxylic group, a polyoxy alkylene group (alkylene of from 2 to 3 carbon atoms), sulfonic acid group, or amino group. Aliphatic fatty acids may be used which will normally be of from about 10 to 36, more usually of from about 12 to 20 carbon atoms. Also, fatty alcohols having the carbon limits indicated for the fatty acids, fatty amines of similar carbon limitations and various steroids may also find use.

The oil droplets can comprise a fluorocarbon oil or a silicone oil (silicon particle). Such droplets are described by Giaever in U.S. Pat. Nos. 4,634,681 and 4,619,904 (the disclosures of which are incorporated herein in their entirety). These droplets are formed by dispersing a fluorocarbon oil or silicone oil in an aqueous phase. The droplets are prepared by placing a small amount of the selected oil (generally, such oils are commercially available) in a container with a larger amount of the aqueous phase. The liquid system is subjected to agitation to bring about emulsification and then centrifuged. The homogeneous phase is removed and the residual droplets are resuspended in an aqueous buffered medium. The above centrifugation and decantation steps can be repeated one or more times before the droplets are utilized.

Catalyst and sbp members can be bound to the droplets in a number of ways. As described by Giaever, supra, the particular sbp member, e.g., a proteinaceous sbp member, can be coated on the droplets by introducing an excess of the sbp member into the aqueous medium prior to or after the emulsification step. Washing steps are desirable to remove excess sbp member. Functionalization of the oil introduces functionalities described above for linking to sbp members.

A chemiluminescent olefin as a label is often chosen to be soluble in the oil phase of the oil droplet. When the oil is a fluorocarbon, a fluorinated chemiluminescent olefin is often more soluble than the corresponding unfluorinated derivation.

Other oil droplets described by Giaever also find use in the present invention.

Liposomes—microvesicles comprised of one or more lipid bilayers having approximately spherical shape and one of the preferred materials for use in the present invention. The liposomes have a diameter that is at least about 20 nm and not more than about 20 microns, usually at least about 40 nm and less than about 10 microns. Preferably, the diameter of the liposomes will be less than about two microns so as to limit settling or floatation.

The outer shell of a liposome consists of an amphiphilic bilayer that encloses a volume of water or an aqueous solution. Liposomes with more than one bilayer are referred to as multilamellar vesicles. Liposomes with only one bilayer are called unilamellar vesicles. Multilamellar vesicles are preferred in the present invention when using a lipophilic chemiluminescent olefin because of their ability to incorporate larger quantities of this material than with unilamellar vesicles. The amphiphilic bilayer is frequently comprised of phospholipids. Phospholipids employed in preparing particles utilizable in the present invention can be any phospholipid or phospholipid mixture found in natural membranes including lecithin, or synthetic glyceryl phosphate diesters of saturated or unsaturated 12-carbon or 24-carbon linear fatty acids wherein the phosphate can be present as a monoester, or as an ester of a polar alcohol such as ethanolamine, choline, inositol, serine, glycerol and the like. Particularly preferred phospholipids include L-a-palmitoyl oleoyl-phosphatidylcholine (POPC), palmitoyl oleoylphosphatidyl-glycerol (POPG), L-a-dioleoylphosphatidylglycerol, L-a(dioleoyl)-phosphatidyl ethanolamine (DOPE) and L-a(dioleoyl)-phosphatidyl -(4-(N-maleimidomethyl)-cyclohexane-1-carboxyamido) ethanol (DOPE-MCC).

The phospholipids in the bilayer may be supplemented with cholesterol and may be replaced with other amphiphilic compounds that have a polar head group, usually charged, and a hydrophobic portion usually comprised of two linear hydrocarbon chains. Examples of such substituents include dialkylphosphate, dialkoxypropylphosphates wherein the alkyl groups have linear chains of 12–20 carbon atoms, N-(2,3-di-(9-(Z)- octa-decenyloxy))-prop-1-yl-N,N,N-trimethyl-ammonium chloride (DOTMA), as disclosed in U.S. patent application Ser. No. 811,146 filed on Dec. 19, 1985, which is hereby incorporated herein by reference, sphingomyelin, cardiolipin, and the like.

Liposomes utilized in the present invention preferably have a high negative charge density to stabilize the suspension and to prevent spontaneous aggregation.

For use in the present invention the liposomes should be capable of binding to a catalyst and be capable of having a label such as a chemiluminescent olefin associated with either the aqueous or the nonaqueous phase.

Liposomes may be produced by a variety of methods including hydration and mechanical dispersion of dried phospholipid or phospholipid substitute in an aqueous solution. Liposomes prepared in this manner have a variety of dimensions, compositions and behaviors. One method of reducing the heterogeneity and inconsistency of behavior of mechanically dispersed liposomes is by sonication. Such a method decreases the average liposome size. Alternatively, extrusion is usable as a final step during the production of the liposomes. U.S. Pat. 4,529,561 discloses a method of extruding liposomes under pressure through a uniform pore-size membrane to improve size uniformity.

Preparation of liposomes containing a chemiluminescent olefin dissolved in the lipid bilayer can be carried out in a variety of methods, including a method described by Olsen, et al., *Biochemica et Biophysica Acta*, 557(9), 1979. Briefly, a mixture of lipids containing the appropriate chemiluminescent olefin in an organic solvent such as chloroform is dried to a thin film on the walls of a glass vessel. The lipid film is hydrated in an appropriate buffer by shaking or vortexing. Thereafter, the lipid suspension is extruded through a series of polycarbonate filter membranes having successively smaller pore sizes. For example, 2.0, 1.0, 0.8, 0.6, 0.4, and 0.2 microns. Repeated filtration through any of the filters, and in particular through the smallest filter, is desirable. The liposomes can be purified by, for example, gel filtration, such as through a column of Sephacryl S-1000. The column can be eluted with buffer and the liposomes collected. Storage in the cold prolongs shelf-life of the liposomes produced by this method. Alternatively, the chemiluminescent olefin can be added to the liquid suspension following preparation of the liposomes.

Liposomes and oil droplets will often have, for example, thiol or maleimide or biotin groups on the molecules comprising the lipid bilayer. Catalyst molecules and sbp members may then be bound to the surface by reaction of the particles with one of these materials that is bound to a sulfhydryl reactive reagent, a sulfhydryl group, or avidin, respectively. Sulfhydryl reactive groups include, among others, activated disulfides such as 2-pyridyl disulfides and alkylating reagents such as bromoacetamide and maleimide.

Catalyst molecules and sbp members can be attracted to the surface of the liposome particles by weak hydrophobic interactions, however such interactions are not generally sufficient to withstand the shear force encountered during incubation and washing. It is preferable to covalently bond catalyst molecules and sbp members to a liposome particle that has been functionalized, for example by use of DOPE-MCC, as shown above, by combining the liposome with the selected catalyst or sbp member functionalized with a mercaptan group. For example, if the sbp member is an antibody, it may be reacted with S-acetyl-mercaptosuccinic anhydride (SAMSA) and hydrolyzed to provide a sulfhydryl modified antibody. Other examples include the N-hydroxysuccinimide ester of surface carboxyl groups, which are then contacted with a linker having amino groups that will react with the ester groups or directly with a catalyst or an sbp member that has an amino group. The linker will usually be selected to reduce nonspecific binding of assay components to the particle surface and will preferably provide suitable functionality for both attachment to the particle and attachment of the catalyst or sbp member. Suitable materials include maleimidated aminodextran (MAD), polylysine, aminosaccharides, and the like. MAD can be prepared as described by Hubert, et al., *Proc. Natl. Acad. Sci.*, 75(7), 3143, 1978.

Latex particles—"Latex" signifies a particulate water suspendible water insoluble polymeric material usually having particle dimensions of 20 nm to 20 $\mu$m, more preferably 100 to 1000 nm in diameter. The latex is frequently a substituted polyethylene such as polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyridine, vinyl-chloride acrylate copolymers, and the like. Non-crosslinked polymers of styrene and carboxylated styrene or styrene functionalized with other active groups such as amino, hydroxyl, halo and the like are preferred. Frequently, copolymers of substituted styrenes with dienes such as butadiene will be used.

The association of the label with latex particles utilized in the present invention may involve incorporation during formation of the particles by polymerization but will usually involve incorporation into preformed particles, usually by noncovalent dissolution into the particles. Usually, a solution of the label will be employed particularly where the label is a chemiluminescent olefin. Solvents that may be utilized include alcohols, including ethanol, ethylene glycol and benzyl alcohol; amides such as dimethyl formamide, formamide, acetamide and tetramethyl urea and the like; sulfoxides such as dimethyl sulfoxide and sulfolane; and ethers such as carbitol, ethyl carbitol, dimethoxy ethane and the like, and water. The use of solvents having high boiling points in which the particles are insoluble permits the use of elevated temperatures to facilitate dissolution of the label compounds into the particles and are particularly suitable. The solvents may be used singly or in combination.

For incorporating chemiluminescent olefins in particles cosolvents that remain permanently in the particles may be used. These solvents serve as plasticizers and are used to enhance luminescence. Frequently, aromatic cosolvents are used including dibutylphthalate, naphthonitrile, dioctylterephthalate, decyldichlorobenzene, diphenylether, dibutoxybenzene, etc; these cosolvents are used at sufficiently low concentrations to avoid dissolution of the particles but at concentrations sufficient to swell the particles.

Generally, the temperature employed during the procedure will be chosen to maximize the singlet oxygen formation and the quantum yield of the chemiluminescent olefin associated with the particles with the proviso that the particles should not melt or become aggregated at the selected temperature. Elevated temperatures are normally employed. The temperatures for the procedure will generally range from 20° C. to 200° C., more usually from 70° C. to 130° C. It has been observed that some compounds that are nearly insoluble at room temperature, are soluble in, for example, low molecular weight alcohols, such as ethanol and ethoxyethanol and the like, at elevated temperatures. Carboxylated modified latex particles have been shown to tolerate low molecular weight alcohols at such temperatures.

A catalyst or an sbp member may be physically adsorbed on the surface of the latex particle or may be covalently bonded or attached to the particle in a manner similar to that discussed above with respect to other matrices.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Polynucleotide—a compound or composition which is a polymeric nucleotide having in the natural state about 50 to 500,000 or more nucleotides and having in the isolated state about 15 to 50,000 or more nucleotides, usually about 15 to 20,000 nucleotides, more frequently 15 to 10,000 nucleotides. The polynucleotide includes nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

Ligand—any organic compound for which a receptor naturally exists or can be prepared.

Ligand analog—a modified ligand, an organic radical or analyte analog, usually of a molecular weight greater than 100, which can compete with the analogous ligand for a receptor, the modification providing means to join a ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, and the like.

Specific binding—the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

Non-specific binding—non-covalent binding between molecules that is relatively independent of specific surface structures. Non-specific binding may result from several factors including hydrophobic interactions between molecules.

Antibody—an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Broughton and Strong, Clin. Chem. 22: 726–732 (1976); and Playfair, et al., Br. Med. Bull. 30: 24–31 (1974).

Antibodies can also be obtained by somatic cell hybridization techniques, such antibodies being commonly referred to as monoclonal antibodies. Monoclonal antibodies may be produced according to the standard techniques of Köhler and Milstein, *Nature* 265: 495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Samples of an appropriate immunogen preparation are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Kohler and Milstein, supra).

In another approach for the preparation of antibodies the sequence coding for antibody binding sites can be replicated from cDNA and inserted into a cloning vector which can be expressed in bacteria to produce recombinant proteins having the corresponding antibody binding sites.

In general, antibodies can be purified by known techniques such as chromatography, e.g., DEAE chromatography, ABx chromatography, and the like, filtration, and so forth.

Alkyl—a monovalent branched or unbranched radical derived from an aliphatic hydrocarbon by removal of one H atom; includes both lower alkyl and upper alkyl.

Lower alkyl—alkyl containing from 1 to 5 carbon atoms such as, e.g., methyl, ethyl, propyl, butyl, isopropyl, isobutyl, pentyl, isopentyl, etc.

Upper alkyl—alkyl containing more than 6 carbon atoms, usually 6 to 20 carbon atoms, such as, e.g., hexyl, heptyl, octyl, etc.

Alkylidene—a divalent organic radical derived from an aliphatic hydrocarbon, such as, for example, ethylidene, in which 2 hydrogen atoms are taken from the same carbon atom.

Aryl—an organic radical derived from an aromatic hydrocarbon by the removal of one atom and containing one or more aromatic rings, usually one to four aromatic rings, such as, e.g., phenyl (from benzene), naphthyl (from naphthalene), etc.

Aralkyl—an organic radical having an alkyl group to which is attached an aryl group, e.g., benzyl, phenethyl, 3-phenylpropyl, 1-naphthylethyl, etc. Alkoxy—an alkyl radical attached to the remainder of a molecule by an oxygen atom, e.g., methoxy, ethoxy, etc.

Aryloxy—an aryl radical attached to the remainder of a molecule by an oxygen atom, e.g., phenoxy, naphthoxy, etc.

Aralkoxy—an aralkyl radical attached to the remainder of a molecule by an oxygen atom, e.g., benzoxy, 1-naphthylethoxy, etc.

Substituted—means that a hydrogen atom of a molecule has been replaced by another atom, which may be a single atom such as a halogen, etc., or part of a group of atoms forming a functionality such as a substituent having from 1 to 50 atoms (other than the requisite hydrogen atoms necessary to satisfy the valencies of such atoms), which atoms are independently selected from the group consisting of carbon, oxygen, nitrogen, sulfur, halogen (chlorine, bromine, iodine, fluorine) and phosphorus, and which may or may not be bound to one or more metal atoms.

Alkylthio—an alkyl radical attached to the remainder of a molecule by a sulfur atom, e.g., methylthio, ethylthio, etc.

Arylthio—an aryl radical attached to the remainder of a molecule by a sulfur atom, e.g., phenylthio, naphthylthio, etc.

Electron-donating group—a substituent which, when bound to a molecule, is capable of polarizing the molecule such that the electron-donating group becomes electron poor and positively charged relative to another portion of the molecule, i.e., has reduced electron density. Such groups include, by way of illustration and not limitation, amines, ethers, thioethers, phosphines, hydroxy, oxyanions, mercaptans and their anions, sulfides, etc.

A substituent having from 1 to 50 atoms (other than the requisite hydrogen atoms necessary to satisfy the valencies of such atoms), which atoms are independently selected from the group consisting of carbon, oxygen, nitrogen, sulfur, halogen and phosphorus—an organic radical; the organic radical has 1 to 50 atoms other than the requisite number of hydrogen atoms necessary to satisfy the valencies of the atoms in the radical. Generally, the predominant atom is carbon (C) but may also be oxygen (O), nitrogen (N), sulfur (S), phosphorus (P), wherein the O, N, S, or P, if present, are bound to carbon or one or more of each other or to hydrogen or a metal atom to form various functional groups, such as, for example, carboxyl groups (carboxylic acids), hydroxyl groups (alcohols), mercapto groups (thiols), carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes and nitrites, and alkyl, alkylidine, aryl, aralkyl, and alkyl, aryl, and aralkyl substituted with one or more of the aforementioned functional groups, e.g., phenyl, naphthyl, phenanthryl, m-methoxyphenyl, dimethylamino, trityl, methoxy, N-morpholeno and may be taken together to form a ring such as, for example, adamantyl, N-methyacridanylide, xanthanylidene, 1-(3,4-benzo-5-hydrofurylidene), and the like.

Linking group—a group involved in the covalent linkage between molecules. The linking group will vary depending upon the nature of the molecules, i.e., label, matrix, catalyst, sbp member or molecule associated with, or part of, a particle being linked. Functional groups that are normally present or are introduced on a matrix, catalyst or an sbp member will be employed for linking these materials.

For the most part, carbonyl functionalities will find use, both oxocarbonyl, e.g., carboxy and aldehyde, and non-oxocarbonyl (including nitrogen and sulfur analogs) e.g., amidine, amidate, thiocarboxy and thionocarboxy.

Alternative functionalities include active halogen, diazo, mercapto, olefin, particularly activated olefin, amino, phosphate esters and the like. A description of linking groups may be found in U.S. Pat. No. 3,817,837, which disclosure is incorporated herein by reference in its entirety.

The linking groups may vary from a bond to a chain of from 1 to 100 atoms, usually from about 1 to 70 atoms, preferably 1 to 50 atoms more preferably 1 to 20 atoms, each independently selected from the group normally consisting of carbon, oxygen, sulfur, nitrogen, halogen and phosphorous. The number of heteroatoms in the linking groups will normally range from about 0 to 20, usually from about 1 to 15, more preferably 2 to 6. The atoms in the chain may be substituted with atoms other than hydrogen in a manner similar to that described above for the substituent having from 1 to 50 atoms. As a general rule, the length of a particular linking group can be selected arbitrarily to provide for convenience of synthesis and the incorporation of any desired group such as an energy acceptor, fluorophor, group for catalysis of intersystem crossing such as a heavy atom, and the like. The linking groups may be aliphatic or aromatic, although with diazo groups, aromatic groups will usually be involved.

When heteroatoms are present, oxygen will normally be present as oxo or oxy, bonded to carbon, sulfur, nitrogen or phosphorous, nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester.

Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

For the most part, when a linking group will have a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or a, b-unsaturated ester. These functionalities will be linked to amine groups, carboxyl groups, active olefins, alkylating agents, e.g., bromoacetyl. Where an amine and carboxylic acid or its nitrogen derivative or phosphoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed.

A group or functionality imparting hydrophilicity or water solubility—is a hydrophilic functionality, which increases wettability of solids with water and the solubility in water of compounds to which it is bound. Such functional group or functionality can be a substituent having 1 to 50 or more atoms and can include a group having a sulfonate, sulfate, phosphate, amidine, phosphonate, carboxylate, hydroxyl particularly polyols, amine, ether, amide, and the like. Illustrative functional groups are carboxyalkyl, sulfonoxyalkyl, $CONHOCH_2COOH$, CO-(glucosamine), sugars, dextran, cyclodextrin, $SO_2NHCH_2COOH$, $SO_3H$, $CONHCH_2CH_2SO_3H$, $PO_3H_2$, $OPO_3H_2$, hydroxyl, carboxyl, ketone, and combinations thereof. Most of the above functionalities can also be utilized as attaching groups, which permit attachment of a catalyst, an sbp member or the like to a particulate composition comprised of the label.

A group or functionality imparting lipophilicity or lipid solubility—is a lipophilic functionality, which decreases the wettability of surfaces by water and the solubility in water of compounds to which it is bound. Such functional group or functionality can contain 1 to 50 or more atoms, usually carbon atoms substituted with hydrogen or halogen and can include alkyl, alkylidene, aryl and aralkyl. The lipophilic group or functionality will normally have one to six straight or branched chain aliphatic groups of at least 6 carbon atoms, more usually at least 10 carbon atoms, and preferably at least 12 carbon atoms, usually not more than 30 carbon atoms. The aliphatic group may be bonded to rings of from 5 to 6 members, which may be alicyclic, heterocyclic, or aromatic. Lipophilic groups may be bonded to a label or other substance to increase its solubility in a non-aqueous matrix.

Energy acceptor—referred to herein also as fluorescent energy acceptor. A chromophore having substantial absorption higher than 310 nm, normally higher than 350 nm, and preferably higher than about 400 nm. The choice of the energy acceptor will also be governed by the particular CC. The energy acceptor should be capable of absorbing light emitted by the CC. Preferably, the absorption maximum of the energy acceptor should be at similar wavelength as the emission maximum of the chemiluminescent olefin. A high extinction coefficient is desirable, usually in excess of 10, preferably in excess of $10^3$, and particularly preferred in excess of $10^4$. The energy acceptor must be fluorescent and will preferably have a high fluorescence quantum yield, usually at least 0.1, preferably greater than 0.4. The energy acceptor simply serves to shift the wavelength of emission and is incorporated in particles containing the CC. Useful energy acceptors are any fluorescent molecule that emits at long wavelengths, preferably, hydrophobic compounds, e.g., phthalocyanines, squaraines, porphyrins, polyacetylenes, naphthacenes, bisphenylethynylanthracene, coumarins, polycyclic aromatic hydrocarbons, etc.

A number of different molecules useful as the energy acceptor are described by Ullman, et al. in U.S. Pat. Nos. 4,261,968, 4,174,384, 4,199,559 and 3,996,345, at columns 8 and 9, the relevant portions of which are incorporated herein by reference.

Another group of fluorescent compounds are the naphthylamines, having an amino group in the alpha or beta position, usually alpha position. Included among the naphthylamino compounds are 1-dimethylaminonaphthalene, 1-anilino-8-naphthalene and 2-p-toluidinyl-6-naphthalene.

The label and energy acceptor, when one is employed, are associated with the matrix of the present invention as described above. As used herein, the term "associated with" includes the following: The association may be through covalent or non-covalent binding or through incorporation into matrix such as a particle. In general, a suspendible particle in which the label is incorporated will have a catalyst bound to it prior to or during the course of the assay.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

As mentioned above, the present compositions find use in methods for detecting hydrogen peroxide or a compound capable of generating hydrogen peroxide. Normally, the assay is carried out by contacting the composition with the assay medium suspected of containing hydrogen peroxide or the compound capable of generating hydrogen peroxide. When hydrogen peroxide is produced from a reaction of an analyte, all the necessary reagents required to cause the reaction to take place are also included in the assay medium. The compositions comprise a matrix, preferably in the form of particles. The matrix has a label incorporated therein and a catalyst bound, or that becomes bound, to its surface. Hydrogen peroxide reacts with the catalyst with the formation of singlet oxygen, which can diffuse into the matrix and react with the label. In the case of a chemiluminescent olefin, a chemiluminescent signal is generated, which is related to the amount of hydrogen peroxide in the medium.

The assay is usually carried out in an aqueous buffered medium at a moderate pH, generally that which provides optimum assay sensitivity. The aqueous medium may be solely water or may include from 0.01 to 80 or more volume percent of a cosolvent. The pH for the medium will usually be in the range of about 4 to 13, more usually in the range of about 5 to 10, and preferably in the range of about 5 to 9, more preferably 6 to 8. The pH is generally selected to achieve optimum assay sensitivity and specificity. Among the factors that must be considered are the pH dependence of the rates of the reactions that produce hydrogen peroxide, the efficiency of formation of singlet oxygen from hydrogen peroxide, the binding of binding members and the minimization of non-specific binding.

Various buffers may be used to achieve the desired pH and maintain the pH during the determination. Illustrative buffers include acetate, borate, phosphate, carbonate, TRIS, barbital and the like. The particular buffer employed is not critical to this invention, but in an individual assay one or another buffer may be preferred.

Moderate temperatures are normally employed for carrying out the assay and usually constant temperature, preferably, room temperature, during the period of the measurement. Incubation temperatures will normally range from about 5° to 99° C., usually from about 15° to 70° C., more usually 20 to 45° C. Temperatures during measurements will generally range from about 10° to 70° C., more usually from about 20° to 45° C., more usually 20° to 25° C.

In some instances the activated CC may require heating to produce luminescence because of its relative stability at ambient temperatures. Relatively stable dioxetanes can be formed, for example, by reaction of singlet oxygen with adamantylidenes (see, e.g., McCapra, supra) and relatively stable endoperoxides can be formed by reaction of singlet oxygen with 1,4-disubstituted naphthacenes (see, e.g., Wilson, J., *J. Am. Chem. Soc.* (1969) 91: 2387). In both circumstances above, the stable materials will undergo decay upon heating, usually, at a temperature of less than 200° C., preferably about 50 to 100° C. Such heating can cause the rapid decomposition of the singlet oxygen/olefin adduct and, thus, the emission of light can occur over a short period of time. The use of this approach may be desirable when detecting very low concentrations of hydrogen peroxide and is discussed in more detail hereinbelow.

The concentration of compound to be detected will generally vary from about $10^{-5}$ to $10^{-17}$ M, more usually from about $10^{-6}$ to $10^{-14}$ M. Considerations, such as whether the assay is qualitative, semiquantitative or quantitative, the particular detection technique and the nature and concentration of the compound of interest will normally determine the concentrations of the various reagents.

While the concentrations of the various reagents in the assay medium will generally be determined by the concentration range of interest of the compound to be detected, the final concentration of each of the reagents will normally be determined empirically to optimize the sensitivity of the assay over the range. That is, a variation in concentration of the compound to be detected which is of significance should provide an accurately measurable signal difference.

While the order of addition may be varied widely, there will be certain preferences depending on the nature of the assay. The simplest order of addition is to add all the materials simultaneously. Alternatively, the reagents can be combined wholly or partially sequentially. One or more incubation steps may be involved after the reagents are combined, generally ranging from about 5 seconds to 1 hour, more usually from about 20 seconds to 10 minutes.

It is desirable for the product of the reaction of singlet oxygen with the chemiluminescent olefin to decay rapidly. The product formed by the activation of the CC with singlet oxygen preferably decomposes spontaneously with emission of light usually with a lifetime of 10 microseconds to 10 hours, preferably 100 microseconds to 10 minutes, more preferably, 300 microseconds to 30 seconds.

One of the factors that allow control of the time to luminescence is the structure of the CC. Structural features that contribute to a delay in luminescence are complex and only partially predictable. Schaap, supra, and McCapra, supra, discuss some of the principles involved and the relevant portions of these references are incorporated herein by reference.

Another factor that allows for control of the time to luminescence is the composition of the particle. In general, when the particle is composed of a non-polar material in which the CC is dissolved decay times and quantum efficiencies are increased relative to polar materials.

Another factor that may be used to control the time to luminescence is temperature. In general, increasing the temperature will decrease the decay time.

Another factor in the control of the time to luminescence is the presence of activators that enhance the rate of decomposition of the dioxetanes produced in the reaction. Such activators include polarizable solvents such as halocarbons, polar compounds such as esters, nitrites, organometallic compounds and the like. The activator is usually present in the matrix in an amount sufficient to achieve the desired delay in time to luminescence. This amount depends on the nature of the activator and generally is about $10^{-5}$ to $10^{-1}$ M.

The chemiluminescence or light produced as a result of the above can be measured visually, photographically, actinometrically, spectrophotometrically or by any other convenient means to determine the amount thereof, which is related to the amount of compound in the medium. Usually, light emitted from the chemiluminescent material is measured while the chemiluminescent material is in contact with the assay medium, for example, by means of a luminometer or a photosensitive material. When a short lived singlet oxygen/olefin adduct, i.e., the product of the reaction of singlet oxygen with a CC, is formed, the light intensity will be nearly proportional to the concentration of hydrogen peroxide in the medium. Where the compound such as hydrogen peroxide is being formed as a result of a reaction of an analyte with assay reagents, the light intensity will increase as the hydrogen peroxide concentration increases.

As mentioned above, in order to detect very small amounts of hydrogen peroxide, a chemiluminescent material is employed that undergoes only slow chemiluminescent decay at ambient temperature following reaction with singlet oxygen. Generally, for very low concentrations of hydrogen peroxide the catalyst coated matrix is incubated with the assay medium for a sufficient period to permit most of the hydrogen peroxide to react with the catalyst to form singlet oxygen, which reacts with the CC that is incorporated in the matrix. During this period there is little or no chemiluminescent emission. Following the incubation, the matrix containing the chemiluminescent material is heated to cause chemiluminescent decomposition of the singlet oxygen adduct. Heating the matrix may be carried out while it is in contact with the reaction medium or the matrix may optionally be separated from the reaction medium. As mentioned above, in this circumstance heating is usually at a temperature of less than 200° C., preferably about 50 to 120° C. Heating causes rapid decomposition of the singlet oxygen/olefin adduct and, thus, the emission occurs over a short period of time. Since a short, high intensity burst of light is more readily detected than a long, low intensity glow that produces the same number of light quanta, this approach provides for more sensitive detection of hydrogen peroxide. Another approach is to use a fluorescent compound precursor and examine the matrix for fluorescence.

One particular application of the methods and compositions of the invention is a method for determining an analyte, which is a member of a specific binding pair (sbp). A combination is provided comprising (i) a sample suspected of containing the analyte, (ii) an first sbp member bound to one of an enzyme pair consisting of an oxidase and a peroxidase, the sbp member being capable of binding to the analyte or to another sbp member capable of binding to the analyte, (iii) a substrate for the oxidase capable of generating hydrogen peroxide upon reaction with the oxidase and (iv) a composition comprising a matrix that permits the diffusion of singlet oxygen therein. The matrix has incorporated a label capable of being modified by singlet oxygen and, on its surface, (1) a second sbp member capable of binding the first sbp member in an amount dependent on the presence of the analyte and optionally (2) the other member of the enzyme pair. When the other member of the enzyme pair is not bound to the matrix, it is included in the assay combination bound to an sbp member that is capable of binding to the matrix. The combination is incubated in a medium under conditions sufficient to allow the sbp members to bind and the substrate for the oxidase to react with the oxidase. A determination is made as to whether singlet oxygen has reacted with the label. The extent of such reaction is related to the presence and/or amount of the analyte in the sample.

The method and compositions of the invention may be adapted to most assays involving sbp members such as ligand-receptor, e.g., antigen-antibody reactions, polynucleotide binding assays, and so forth. The assays are usually homogeneous or heterogeneous, preferably homogeneous, including competitive and sandwich. In a specific binding assay, the sample may be pretreated, if necessary, to remove unwanted materials.

As mentioned previously, the first sbp member above is capable of binding to the analyte or to an sbp member capable of binding to the analyte. When the second sbp member is also capable of binding to the analyte, a sandwich assay protocol can result. The immunological reaction for a sandwich type assay usually involves an sbp member, e.g., an antibody, that is complementary to the analyte, a second sbp member, e.g., antibody, that is also complementary to the analyte and bound to the particulate matrix, and the sample of interest.

One of the sbp members alternatively can be analogous to the analyte, in which case a competitive assay protocol can result. The immunological reaction for a competitive protocol usually involves an sbp member that is complementary to the analyte and an sbp member that is analogous to, usually a derivative of, the analyte. One of these sbp members will be associated with the matrix.

In one type of assay, a sample suspected of containing an analyte, which is an sbp member and the other assay components comprising an enzyme bound to an sbp member and a substrate are combined with a particulate matrix of the present invention. The medium is then examined for the presence of chemiluminescent emission, usually by measuring the amount of light emitted, which is related to the amount of analyte in the sample. This approach is a homogeneous assay where a separation step is not employed. Alternatively, a particulate or non-particulate matrix may be used, which, after combining the assay components, may be separated from the liquid phase, and either the solid phase or the liquid phase may then be examined for the presence of chemiluminescent emission.

An assay for the analyte will normally be carried out in an aqueous buffered medium at a moderate pH, generally that which provides optimum assay sensitivity. In general, the parameters set forth above for assay medium, pH, temperature, and so forth, apply to the assay for an analyte in accordance with the present invention.

Preferred compositions in accordance with the present invention are latex particles or liposomes having incorporated therein a chemiluminescent olefin that reacts with singlet oxygen. A peroxidase, such as a lactoperoxidase or a haloperoxidase, is bound to the surface of the latex particle or liposome.

The following compositions and assays are provided by way of illustration and not limitation to enable one skilled in the art to appreciate the scope of the present invention and to practice the invention without undue experimentation. It will be appreciated that the choice of analytes, labels, catalysts, particles, other reagents and reaction conditions will be suggested to those skilled in the art in view of the disclosure herein and the examples that follow.

In an assay for the detection of hydrogen peroxide, a sample suspected of containing hydrogen peroxide is combined in 1 mL of a 50 mM phosphate buffer (pH ) with 300 nm latex beads having incorporated therein the label 4-(N,N-dioctadecylcarboxamidomethoxy)-benzal acridan (prepared as described in U.S. Pat. No. 5,340,716 at column 51, lines 3–15, and column 48, lines 24–44) at a level of 5% weight/weight (w/w). The latex beads have lactoperoxidase (LP) bound to their surfaces (1000 molecules of LP/bead). The medium, which contains 10 mM sodium bromide is held at 25° C. for 1 minute and the light emitted by the medium is measured. The amount of light emitted by the medium is directly related to the amount of hydrogen peroxide in the sample.

In an assay for the measurement of glucose, a sample (10 $\mu$L) is combined in 1 mL of phosphate buffer (pH about 8) with 200 $\mu$L of glucose oxidase (2.6 $\mu$g/mL) and multilamellar liposomes having incorporated in their bilayers 2-methoxyvinylpyrene and having bound to their surface a chloroperoxidase. The buffered medium also includes 0.1 M sodium chloride. The medium is held at 37° C. for 5 minutes and the luminescence intensity is measured by means of a luminometer. The amount of luminescence is directly related to the amount of glucose in the sample.

In an assay for the measurement of cholesterol, a sample (10 $\mu$L) is combined in 1 mL of phosphate buffer (pH about 8) with 200$\mu$L of cholesterol oxidase (0.2 $\mu$g/mL) and oil droplets comprised of dodecylnaphthalene having incorporated therein 8% w/w 9-(benzal-9H-xanthene). The oil droplets have associated with their surface a chloroperoxidase to which naphthalene is bound through a dodecamethylene spacer. The buffered medium also includes 0.M sodium chloride. The medium is held at 25° C. for 30 minutes and fluorescence is then measured photometrically by means of a fluorometer. In this example, the singlet oxygen produced in accordance with the present invention reacts with the xanthene to give a xanthone, which is fluorescent. The amount of fluorescence is directly related to the amount of cholesterol in the sample.

As explained above, the assay method of the present invention may be applied to the detection of analytes other than hydrogen peroxide and compounds capable of producing hydrogen peroxide. An example, by way of illustration and not limitation, is an assay for the detection of theophylline in a serum sample suspected of containing theophylline. The serum sample (2 $\mu$L) is combined with an assay medium comprising 1 mL of a 50 mM phosphate buffer and 20–40 $\mu$g of 300 nm latex beads having incorporated therein the label 4-(N,N-dioctadecylcarboxamidomethoxy)-benzal acridan (prepared as described in U.S. Pat. No. 5,340,716 at column 51, lines 3–15, and column 48, lines 24–44) at a level of 5% weight/weight (w/w). Bound to the surfaces of the latex beads are lactoperoxidase (LP) (1000 molecules of LP/bead) and anti-theophylline antibody (10 $\mu$g of antibody per mg of beads). The assay medium also contains (i) a conjugate of theophylline covalently bound to the enzyme galactose oxidase (concentration is optimized in the range of $3.2 \times 10^{-12}$ to $3.2 \times 10^{-10}$ moles) and (ii) $\beta$-D-galactose as a substrate for the galactose oxidase (1.0 mM) and (iii) 50 mM sodium bromide as a substrate for LP. The assay medium is incubated at a temperature of 37° C. for a period of 15 minutes and the amount of light emitted by the medium is directly related to the amount of theophylline in the sample.

The above assay functions in the following manner: The theophylline-galactose oxidase conjugate and the sample theophylline compete for the binding sites on the anti-theophylline antibody. Conjugate that binds to the antibody causes the oxidase enzyme to come into close proximity to the LP on the latex particles. The galactose oxidase acts upon its substrate $\beta$-D-galactose to produce hydrogen peroxide and D-galactono-$\delta$-lactone. The LP acts upon the hydrogen peroxide to produce singlet oxygen, which is formed at the surface of, and diffuses into, the latex particle where it reacts with the label 4-(N,N-dioctadecylcarboxamidomethoxy)-benzal acridan causing the production of light. In the above assay the hydrogen peroxide is produced as part of a signal producing system involved in the detection of the theophylline analyte. In the presence of sample theophylline, less light is obtained because the sample theophylline competes with the conjugate for the binding sites on the anti-theophylline antibody. The greater the amount of theophylline in the sample, the lesser the amount of conjugate that binds to the latex particles, the lesser the amount of hydrogen peroxide that forms in the proximity of the LP on the latex, and the lesser the amount singlet oxygen that diffuses into the latex particle to react with the acridan label.

Another example, by way of illustration and not limitation, of the use of the present invention in the detection of an analyte is an assay for the detection of human chorionic gonadatropin (HCG) in a urine sample suspected of containing HCG. The sample (100 $\mu$L) is combined with an assay medium comprising 1 mL of a 50 mM phosphate buffer and 300 nm multilamellar liposomes having incorporated in their bilayers 2-methoxyvinylpyrene and having bound to their surface (i) a chloroperoxidase (CLP) (1000 molecules of CLP/bead) and (ii) antibody to the $\beta$-subunit of HCG. The assay medium also contains (i) 0.1 M sodium chloride and (ii) platinum particles having antibodies to the $\alpha$-subunit of HCG bound thereto (produced as described in U.S. Pat. No. 5,384,265) and (iii) 50 mM hydrazine. The assay medium is incubated at a temperature of 37° C. for a period of 15 minutes and the luminescence intensity is measured by means of a luminometer. The amount of luminescence is directly related to the amount of HCG in the sample The above assay functions in the following manner: The HCG antibodies bind to any HCG molecules in the sample, which causes the platinum particles to come into close proximity to the liposomes. Platinum catalyses the oxidation of hydrazine with production of hydrogen peroxide, which in turn results in the production of singlet oxygen near the surface of the liposomes by virtue of the CLP on the surface of the liposomes. The singlet oxygen diffuses into the liposomes where it reacts with the label 2-methoxyvinylpyrene causing the production of luminescence. In the above assay the hydrogen peroxide is produced as part of a signal producing system involved in the detection of the HCG analyte.

Another aspect of the present invention relates to kits useful for conveniently performing an assay method of the invention for determining the presence or amount of a compound capable of generating hydrogen peroxide, or of an analyte in a sample suspected of containing such compound or analyte. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. The kits comprise in packaged combination (a) a composition comprising a matrix having incorporated therein a label capable of being modified by singlet oxygen, wherein an enzyme capable of catalyzing the conversion of hydrogen peroxide to singlet oxygen is bound to the matrix or, if not so bound, is bound to an sbp member that is capable of binding to the matrix and the matrix permits the diffusion of singlet oxygen therein. The kit also includes a substrate for the enzyme other than hydrogen peroxide. The kit can further include other separately packaged reagents for conducting an assay such as an energy acceptor incorporated in the matrix or bound to an sbp member, additional sbp members, ancillary reagents such as an ancillary enzyme substrate, and so forth. Alternatively, the kit can comprise in packaged combination (a) a composition comprising a matrix and a label capable of being modified by singlet oxygen, (b) a peroxidase and (c) an oxidase wherein the oxidase may be an enzyme or other catalyst capable of producing hydrogen peroxide. The peroxidase and the oxidase are bound to, or capable of becoming bound to, the matrix.

The relative amounts of the various reagents in the kits can be varied widely to provide for concentrations of the reagents which substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

EXAMPLES

The invention is demonstrated further by the following illustrative examples. Parts and percentages recited herein are by weight unless otherwise specified. Temperatures are in degrees centigrade (°C.).

Abbreviations and Materials sec—seconds
hr—hours
min—minutes
RLU—relative light units
rpm—rotations per min
EDTA—ethylenediaminetetraacetic acid
MES—2-[N-morpholino]ethanesulfonic acid
CMO—carboxymethoxylamine hemihydrochloride
NaOAc—sodium acetate
DMF—dimethylformamaide
Dextran T-500 from Pharmacia, catalog #17-0320-02.
Sodium hydroxide from Mallinckrodt AR (lot 7707 KMRT)
Water (deionized) from a Millipore Filtration Unit.
Minikros Lab System (Microgon Inc. cat. # SYLS 121 01N) and Minikros tangential flow modules (M25S 300 01N, M25S 600 01N, M21M-300-01N), both from Microgon Inc. Laguna Hills, Calif.
Disodium ethylene diamine tetraacetic acid, EDTA $Na_2$ from Sigma (cat. # E4884).
Bovine Serum Albumin (BSA) from Sigma (cat. # A7888).
Gentamicin sulfate from GIBCO (cat. #15750-011).
Kathon from Rohm & Haas, part #5A033, lot C1.
NaOH (pellets), 0.1 N NaOH, HCl (conc.), $H_2SO_4$ (conc.) and 0.1 N HCl all from Mallinckrodt (AR grade).
Boric Acid ($H_3BO_3$, granular), acetic acid (glacial, AcOH) and sodium acetate (NaOAc), all from Mallinckrodt (AR grade).
Ethanol (200 proof, EtOH) from Quantum.
p-Dimethylamino benzaldehyde from Sigma (cat. # D-2004)
Streptavidin from Aaston, Inc., (cat. #1 STA-1G-D), or Boehringer Mannheim (cat. #1520679103).
Tween-20 (Surfact-Amps 20) from Pierce Chemical Company.
Particle size was determined by dynamic light scattering on a Nicomp (model 370).
TRIS—Tris(hydroxymethyl)aminomethane-HCl (a 10X solution) from BioWhittaker, Walkersville, Md., or from J. T Baker (cat. #4099-02).
Buffer A—0.1 M, pH 5.0 acetate buffer; 0.2 M solution of sodium acetate (16.4 g) dissolved in 2.0 L of water combined with 0.2 M acetic acid to pH 5.0; diluted with an equal volume of water to give 0.1 M acetate buffer at pH 5.0.
Buffer B—protein free buffer for washing streptavidin coated beads; 121.1 g of TRIS, 175.3 g of NaCl, 93.0 g of EDTA $Na_2.2H_2O$ and 10.0 g of dextran T-500 in 10.0 L of water; adjusted to pH to 8.3 with concentrated HCl.
Buffer C—121.1 g of TRIS (0.1 M), 175.3 g of NaCl (0.3 M), 93.0 g of EDTA $Na_2.2H_2O$ (25 mM), 10.0 g of Dextran T-500 (0.1%), 31.25 ml of HBR-1 (from Scantibodies Laboratory Inc., Los Angeles, Calif.) (1/320), 10.0 g of RIA grade BSA (0.1%), 5 mL of Kathon (0.05%) and 20 mL of Gentamicin sulfate (0.01%) in 10.0 L of water; adjusted to pH to 8.3 with concentrated HCl.

Example 1

Preparation of Lactoperoxidase-coated Chemiluminescer Particles

A. C-28 thioxene was prepared as follows

To a solution of 4-bromoaniline (30 g, 174 mmol) in dry DMF (200 mL) was added 1-bromotetradecane (89.3 mL, 366 mmol) and N,N-diisopropylethylamine (62.2 mL, 357 mmol). The reaction solution was heated at 90° C. for 16 hr under argon before being cooled to room temperature. To this reaction solution was again added 1-bromotetradecane (45 mL, 184 mmol) and N,N-diisopropylethylamine (31 mL, 178 mmol) and the reaction mixture was heated at 90° C. for another 15 hr. After cooling, the reaction solution was concentrated in vacuo and the residue was diluted with $CH_2Cl_2$ (400 mL). The $CH_2Cl_2$ solution was washed with 1 N aqueous NaOH (2x), $H_2O$, and brine, was dried over $Na_2SO_4$ and was concentrated in vacuo to yield a dark brown oil (about 110 g). Preparative column chromatography on silica gel by a Waters 500 Prep LC system eluting with hexane afforded a yellow oil that contained mainly the product (4-bromo-N,N-di-($C_{14}H_{29}$)-aniline) along with a minor component 1-bromotetradecane. The latter compound was removed from the mixture by vacuum distillation (bp 105–110° C., 0.6 mm) to leave 50.2 g (51%) of the product as a brown oil. To a mixture of magnesium turnings (9.60 g, 395 mmol) in dry THF (30 mL) under argon was added dropwise a solution of the above substituted aniline product (44.7 g, 79 mmol) in THF (250 mL). A few crystals of iodine were added to initiate the formation of the Grignard reagent. When the reaction mixture became warm and began to reflux, the addition rate was regulated to maintain a gentle reflux. After addition war complete, the mixture was heated at reflux for an additional hour. The cooled supernatant solution was transferred via cannula to an addition funnel and added dropwise (over 2.5 hr) to a solution of phenylglyoxal (11.7 g, 87 mmol) in THF (300 mL) at −30° C. under argon. The reaction mixture was gradually warmed to 0° C. over 1 hr an stirred for another 30 min. The resulting mixture was poured into a mixture of ice water (800 mL) and ethyl acetate (250 mL). The organic phase was separated and the aqueous phase was extracted with ethyl acetate (3×). The combined organic phases were washed with $H_2O$ (2×), brine and was dried over $MgSO_4$. Evaporation of the solvent gave 48.8 g of the crude product as a dark green oily liquid. Flash column chromatography of this liquid (gradient elution with hexane, 1.5:98.5, 3:97, 5:95 ethyl acetate:hexane) afforded 24.7 g (50%) of the benzoin product (MS ($C_{42}H_{69}NO_2$): [M—H]$^+$618.6, $^1$H NMR (250 MHz, $CDCl_3$) was consistent with the expected benzoin product. To a solution of the benzoin product from above (24.7 g, 40 mmol) in dry toluene (500 mL) was added sequentially 2-mercaptoethanol (25 g, 320 mmol) and TMSCI (100 mL, 788 mmol). The reaction solution was heated at reflux for 23 hr under argon before being cooled to room temperature. To this was added additional TMSCI (50 mL, 394 mmol); and the reaction solution was heated at reflux for another 3 hr. The resulting solution was cooled, was made basic with cold 2.5 N aqueous NaOH and was extracted with $CH_2Cl_2$ (3×). The combined organic layers were washed with saturated aqueous $NaHCO_3$ (2×) and brine, was dried over $Na_2SO_4$ and was concentrated in vacuo to give a brown oily liquid. Preparative column chromatography on silica gel by using a Waters 500 Prep LC system (gradient elution with hexane, 1:99, 2:98 ethyl acetate:hexane) provided 15.5 g (60%) of the C-28 thioxene as an orange-yellow oil (MS ($C_{44}H_{71}NOS$): [M—H]$^{b+}$661.6, $^1$H NMR (250 MHz, $CDCl_3$) was consistent with the expected C-28 thioxene product 2-(4-(N,N-di-($C_{14}H_{29}$)-anilino)-3-phenyl thioxene.

B. Chemiluminescer Beads were Prepared as Follows

The starting beads were carboxylate modified latex purchased from Seradyn Particle Technology, Indianapolis, Ind. The beads contained Eu(TTA)$_3$DPP prepared as follows: DPP/Eu(TTA)$_3$ was prepared by combining 8.69 g of Eu(TTA)$_3$. 3H$_2$O (10 mmoles, Kodak Chemical Company, Rochester N.Y.) and 1.8 g of 1,10-phenanthroline (10 mmoles, Aldrich) in 50 ml of dry toluene and heating to 95° C. in an oil bath for one 1 hr. Toluene was removed under reduced pressure. The ash coloured solid was cystallized from 10 ml of toluene to yield 10 grams of DPP/Eu(TTA)$_3$. Absorption spectrum: 270 nm (20,000), 340 nm (60,000) (Toluene) 1.R(KBr): cm$^{-1}$: 3440(s), 1600(s), 1540(s), 1400 (s), 1300(s). Four mL of 20% suspension (400 mg) of washed 175 nm carboxylate modified latex was diluted with 3 mL of ethoxyethane in a 25 mL round bottom (R.B.) flask with a stir bar. The R.B. flask was then placed in an oil bath at 105° C. and stirred for 10 min. Then, 3.3 mM C-28 thioxene and 15.5 mM Eu(TTA)$_3$DPP was added; the beads were stirred for 5 min more. At this point 1.0 mL of 0.1 N NaOH was added slowly over 5 min. During all the additions, the oil bath temperature was maintained at 105° C. The oil bath temperature was slowly allowed to drop to room temperature over 2 hr. After cooling, the mixture was diluted with 20 mL of ethanol and centrifuged (12,500 rpm, 30 min). Supernatants were discarded and the pellets resuspended in ethanol by sonication. Centrifugation was repeated, and the pellet was resuspended in water; and centrifugation was repeated. The pellet was resuspended in 5 mL of aqueous ethanol to a final volume of 40 mL.

C. Streptavidin Coated Chemiluminescer Beads were Prepared as Follows

Streptavidin from Aaston was a lyophilized white powder containing streptavidin, potassium phosphate, sodium chloride and lactose. The lactose was removed by dialysis against 10 mM $Na_2HPO_4/NaH_2PO_4$ at pH 7.0. A solution of streptavidin at 10–12 mg/mL (75–62.5 mL) was prepared in Buffer A (pH 5.0, 0.2 M).

Aldehyde groups were introduced onto the surface of chemiluminescer beads, prepared as described above, to give aldehyde-chemiluminescer beads. See, for example, U.S. Pat. No. 4,264,766 particularly at column 7, lines 18–42, and column 8, line 63, to column 9, line 25, and U.S. Pat. No. 4,801,504 particularly at column 6, lines 42–50, the relevant portions of both of the above patents being incorporated herein by reference thereto.

A 20 mg/mL solution of aldehyde-chemiluminescer beads containing Tween-20 (75 mL) was prepared. The solution containing the beads was added slowly with gentle stirring to the streptavidin solution, prepared above, contained in a 250 mL glass bottle. A fresh solution of NaCNBH$_3$ in water was prepared and added to the reaction mixture. The final concentration of the reaction mixture was 10 mg/mL in beads, 5 mg/mL in streptavidin, 1.0 mg/mL in NaCNBH$_3$ and 0.1% in Tween-20. The pH of the reaction mixture was adjusted to 5.0. The bottle was shielded from light and shaken at 100–150 rpm at 37° C. for 48–60 hr. The resulting beads were treated to block remaining free aldehyde groups. See, for example, Margel, S., *J. Chromatogr.* (1989) 46: 177–189. The beads were then subjected to ultrafiltration on the Microgon (0.05$\mu$ pore, 1188cm$^2$), first with Buffer B to remove protein and then with Buffer C. The size of the beads was determined on the Nicomp and was approximately 280 nm (intensity weighted) in Buffer C.

D. Preparation of Lactoperoxidase-coated Chemiluminescer Beads

Strepavidin coated chemiluminescer beads (30 mgs) prepared as described above in 1.0 ml of pH 6.0, 10 mM MES buffer were sonicated. 1.0 ml of 1.0 mg/ml biotin labeled lactoperoxidase (Sigma L-8257; 108 units/mg of protein; 6 biotinis/enzyme) in pH 6.0, 10 mM MES buffer was added to the above solution. The reaction mixture was vortexed and incubated at room temperature for 90 min. The chemiluminescer beads were centrifuged and washed three times with 10 ml of pH 6.0,10 mM MES buffer. The chemiluminescer beads were finally resuspended at 1.0 mg/ml in pH 6.0, 10 mM MES buffer with 1.0 mg/ml BSA. The particles were used for the assay.

Example 2

Effect of pH on Chemiluminescent Signal from Lactoperoxidase Bound to Chemiluminescer Particles A solution containing 0.1 mM hydrogen peroxide in different buffers (pH 4.2 and pH 5.0, 0.1 M, acetate and pH 6.0, pH 7.0, pH 7.4 and pH 8.0, 0.1 M phosphate) was prepared. To 1.0 ml of the above solution in a glass tube (12×75 mm) was added 0.01 ml of 1.0 M sodium bromide in deionised water and 0.01 ml of lactoperoxidase coated chemiluminescer particles (1 mg/ml in 10 mM MES buffer pH 6.0). The solution was promptly mixed and tube inserted into a chemiluminometer. The chemiluminescence was integrated for 30 sec. The results are summarized in Table 1.

TABLE 1

| Buffer | pH | RLU (30 sec) (average of 3 readings) |
|---|---|---|
| Acetate | 4.2 | 19000 |
| Acetate | 5.0 | 34000 |
| Phosphate | 6.0 | 65400 |
| Phosphate | 7.0 | 42000 |
| Phosphate | 7.4 | 26000 |
| Phosphate | 8.0 | 20000 |

Example 3

Effect of Sodium Bromide Concentration on Chemiluminescent Signal from Lactoperoxidase Bound to Chemiluminescer Particles A solution containing 0.1 mM hydrogen peroxide in pH 6.0, 0.1 M phosphate buffer was prepared. To 1.0 ml of the above solution in a glass tube (12×75mm) was added 0.0003 ml to 0.06 ml of 1.0 M sodium bromide in deionised water and 0.05 ml of lactoperoxidase coated chemiluminescer particles (1 mg/ml in 10 mM MES buffer pH6.0). The solution was promptly mixed and tube inserted into a chemiluminometer. The chemiluminescent was integrated for 30 sec. The results are summarized in Table 2.

TABLE 2

| Sodium bromide (mM) | RLU (30 sec) (average of 3 readings) |
|---|---|
| 0 | 6122 |
| 3 | 659000 |
| 6 | 1070000 |
| 10 | 1280000 |
| 15 | 1160000 |
| 20 | 1100000 |
| 30 | 914000 |
| 60 | 717000 |

Example 4

Determination of Hydrogen Peroxide

A sample or calibrator containing hydrogen peroxide was prepared in pH 6.0, 0.1 M potassium phosphate buffer (final concentration). To 1 ml of this solution in a glass tube (12×75 mm) was added 0.02 ml of 1.0 M sodium bromide in deionized water and 0.01 ml of the enclosed reagent which contains a suspension of 1 mg/ml of lactoperoxidase coated chemiluminescer particles in MES buffer, pH 6.0. The solution was promptly mixed and the tube inserted into a chemiluminometer. The chemiluminescent signal was integrated over 5 sec. The results are summarized in Table 3.

TABLE 3

| Hydrogen peroxide (mM) | RLU (5 sec) (average of 3 readings) |
|---|---|
| 0.0 | 100 |
| 0.5 | 250 |
| 1.0 | 400 |
| 2.0 | 760 |
| 4.0 | 1400 |
| 6.0 | 2060 |
| 8.0 | 2800 |

Example 5

Determination of Glucose

A sample or calibrator containing glucose was prepared in pH 6.0, 0.1 M potassium phosphate buffer (final concentration) and 0.02 ml of glucose oxidase (1 mg/ml) is added. After mixing, the solution was incubated for 5 min.

To 1 ml of this solution in a glass tube (12×75 mm) was added 0.02 ml of 1.0 M sodium bromide in deionized water and 0.01 ml of the enclosed reagent which contains a suspension of 1 mg/ml of lactoperoxidase coated chemiluminescer particles in MES buffer, pH 6.0. The solution is promptly mixed and the tube inserted into a chemiluminometer. The chemiluminescent signal is integrated over 5 sec. The results are summarized in Table 4.

TABLE 4

| Glucose $\mu$gs/ml | RLU (5 sec) (average of 3 readings) |
|---|---|
| Buffer* | 40 |
| 0 | 110 |
| 1 | 314 |
| 2 | 658 |
| 3 | 962 |
| 5 | 1800 |
| 10 | 4200 |
|  | 12422 (10 min, 1st step) |
|  | 20298 (20 min, 1st step) |

*no chemiluminescer beads

The above discussion includes certain theories as to mechanisms involved in the present invention. These theories should not be construed to limit the present invention in any way, since it has been demonstrated that the present invention achieves the results described.

Although the foregoing invention has been described in some detail by way of illustration and example for purposes of clarity and understanding, it will be obvious that certain changes or modifications may be practiced within the scope of the appended claims.

What is claimed is:

1. A composition comprising a matrix having incorporated therein a label capable of being modified by singlet oxygen, wherein a non-photoactivatable catalyst capable of catalyzing the formation of singlet oxygen from hydrogen peroxide is bound to the surface of said matrix, said matrix permitting the diffusion of singlet oxygen therein.

2. The composition of claim 1 wherein said matrix is selected from the group consisting of polymeric materials, lipid bilayers, oil droplets and cells.

3. The composition of claim 1 wherein said label becomes fluorescent or chemiluminescent upon reaction with singlet oxygen.

4. The composition of claim 1 wherein said label is an olefin.

5. The composition of claim 1 wherein said catalyst is an enzyme.

6. A composition comprising a matrix selected from the group consisting of latex polymers and lipid bilayers, said matrix having incorporated therein a label capable of being activated by singlet oxygen, wherein a peroxidase is bound to the surface of said matrix, said matrix permitting the diffusion of singlet oxygen therein.

7. The composition of claim 6 wherein said matrix is a latex particle.

8. The composition of claim 6 wherein said matrix is a liposome.

9. The composition of claim 6 wherein said label is an olefin capable of reacting with single oxygen to produce chemiluminescence.

10. The composition of claim 6 wherein said label is capable of reacting with singlet oxygen to form a fluorescent product.

11. The composition of claim 6 wherein said peroxidase is a lactoperoxidase or a haloperoxidase.

12. A method for detecting hydrogen peroxide or a compound capable of generating hydrogen peroxide, said method comprising:
(a) providing in combination (i) a sample suspected of containing hydrogen peroxide or said compound and (ii) a composition comprising a matrix having incorporated therein a label capable of being activated by singlet oxygen, wherein a non-photoactivatable catalyst capable of catalyzing the formation of singlet oxygen from hydrogen peroxide is bound to said matrix, said matrix permitting the diffusion of singlet oxygen therein,
(b) subjecting said combination to conditions wherein said catalyst generates singlet oxygen and
(c) determining the luminescence produced by reaction of said singlet oxygen with said label, the reaction thereof indicating the presence of said compound.

13. The method of claim 12 wherein said matrix is selected from the group consisting of polymeric materials, lipid bilayers, oil droplets and cells.

14. The method of claim 12 wherein said label is a chemiluminescent olefin capable of reacting with singlet oxygen to form a dioxetane.

15. The method of claim 12 wherein said catalyst is an enzyme.

16. The method of claim 12 wherein said catalyst is a peroxidase.

17. The method of claim 12 wherein said determining of step (c) is carried out by detecting light emitted by the product of the reaction of said luminescent compound precursor with singlet oxygen.

18. A method for detecting hydrogen peroxide or a substance capable of generating hydrogen peroxide, said method comprising:
(a) providing in combination (i) a sample suspected of containing hydrogen peroxide or a substance capable of generating hydrogen peroxide and (ii) a composition comprising a matrix having incorporated therein a label capable of being activated by singlet oxygen, wherein a non-photoactivatable catalyst capable of catalyzing the conversion of hydrogen peroxide to singlet oxygen is bound to the surface of said matrix, said matrix permitting the diffusion of singlet oxygen therein,
(b) subjecting said combination to conditions wherein hydrogen peroxide reacts with said catalyst to form singlet oxygen and
(c) determining whether singlet oxygen has reacted with said label, the extent of reaction thereof indicating the presence or amount of hydrogen peroxide or of said substance in said sample.

19. The method of claim 18 wherein said substance is a substrate for an oxidase.

20. The method of claim 18 wherein said matrix is selected from the group consisting of organic polymers and lipid bilayers.

21. The method of claim 18 wherein said label is an olefin capable of reacting with singlet oxygen to form a dioxetane.

22. The method of claim 18 wherein said label is a telluride capable of reaction with singlet oxygen to form a fluorescent olefin.

23. The method of claim 18 wherein said catalyst is an enzyme.

24. The method of claim 18 wherein said determining of step (c) is carried out by detecting light emitted by the product of reaction of said label with singlet oxygen.

25. A method for detecting hydrogen peroxide or a substance capable of generating hydrogen peroxide, said method comprising:
(a) providing in combination (i) a sample suspected of containing hydrogen peroxide or a substance capable of generating hydrogen peroxide and (ii) a composition comprising a matrix selected from the group consisting of latex polymers and lipid bilayers, said matrix having incorporated therein an olefin capable of reaction with singlet oxygen, wherein a peroxidase is bound to the surface of said matrix, said matrix permitting the diffusion of singlet oxygen therein,
(b) subjecting said combination to conditions wherein hydrogen peroxide reacts with said peroxidase to form singlet oxygen and
(c) determining whether singlet oxygen has reacted with said olefin, the reaction thereof indicating the presence of hydrogen peroxide or of said substance in said sample.

26. The method of claim 25 wherein said substance is selected from the group consisting of cells, substrates for an oxidase and precursors of a substrate for an oxidase.

27. The method of claim 26 wherein said substrate for an oxidase is selected from the group consisting of saccharides, alcohols, amines, NADH, xanthene, uric acid and cholesterol.

28. The method of claim 25 wherein said matrix is a latex polymer particle.

29. The method of claim 25 wherein said matrix is a liposome.

30. The method of claim 25 wherein said olefin is capable of reacting with single oxygen to form a dioxetane.

31. The method of claim 25 wherein said peroxidase is a lactoperoxidase or a haloperoxidase.

32. The method of claim 25 wherein said determining of step (c) is carried out by detecting light emitted by the product of reaction of said olefin with singlet oxygen.

33. A method for detecting an analyte, said analyte being a member of a specific binding pair (sbp), said method comprising:
(a) providing in combination in a medium (i) a sample suspected of containing said analyte, (ii) an sbp member bound to one of an oxidase or a peroxidase, said sbp member being capable of binding to said analyte or to an sbp member capable of binding to said analyte, (iii) a composition comprising a matrix having incorporated therein a label capable of being modified by singlet oxygen, said matrix permitting the diffusion of singlet oxygen therein, (iv) the other of said oxidase or said peroxidase bound to said matrix or bound to an sbp member capable of binding to said matrix and (v) a substrate for said oxidase capable of generating hydrogen peroxide upon reaction with said oxidase and (b) incubating said medium under conditions sufficient to allow said sbp members to bind and said substrate for said oxidase to react with said oxidase and (c) determining whether singlet oxygen has reacted with said label, the extent of reaction thereof being related to the presence and/or amount of said analyte in said sample.

34. The method of claim 33 wherein said analyte is selected from the group consisting of cell surface antigens, small organic compounds, poly(amino acids) and polynucleotides.

35. The method of claim 33 wherein said substrate for an oxidase is a saccharide.

36. The method of claim 33 wherein said matrix is a latex particle.

37. The method of claim 33 wherein said matrix is a liposome.

38. The method of claim 33 wherein said label is capable of reacting with single oxygen to produce chemiluminescence.

39. The method of claim 33 wherein said label is capable of reacting with singlet oxygen to form a fluorescent product.

40. The method of claim 33 wherein said peroxidase is a lactoperoxidase or a haloperoxidase.

41. The method of claim 33 wherein said peroxidase is bound to said matrix.

42. A kit comprising in packaged combination:

(a) a composition comprising a matrix having incorporated therein a label capable of being modified by singlet oxygen, wherein a first enzyme capable of catalyzing the conversion of hydrogen peroxide to singlet oxygen is bound to said matrix or to an sbp member that is capable of binding to said matrix, said matrix permitting the diffusion of singlet oxygen therein, and (b) an oxidase.

43. The kit of claim 42 wherein said matrix is selected from the group consisting of organic polymers and lipid bilayers and wherein said oxidase is bound to an sbp member.

44. The kit of claim 42 wherein said label is a chemiluminescent olefin capable of reacting with singlet oxygen.

45. The kit of claim 42 wherein said enzyme is a peroxidase.

46. A kit comprising in packaged combination:

(a) a composition comprising a matrix having incorporated therein a label capable of being modified by singlet oxygen, (b) a peroxidase and (c) an oxidase, wherein said peroxidase and said oxidase are bound to said matrix or a member of a specific binding pair capable of becoming bound to said matrix.

47. The kit of claim 46 wherein both said peroxidase and said oxidase are each separately bound to said member of a specific binding pair.

* * * * *